US011806103B2

(12) United States Patent
Kawabata et al.

(10) Patent No.: US 11,806,103 B2
(45) Date of Patent: Nov. 7, 2023

(54) ROBOTIC SURGICAL SYSTEM AND DISPLAY METHOD

(71) Applicants: MEDICAROID CORPORATION, Kobe (JP); KAWASAKI JUKOGYO KABUSHIKI KAISHA, Kobe (JP)

(72) Inventors: Hideo Kawabata, Kobe (JP); Takaki Morimoto, Yokohama (JP)

(73) Assignees: MEDICAROID CORPORATION, Kobe (JP); KAWASAKI JUKOGYO KABUSHIKI KAISHA, Kobe (JP)

( * ) Notice: Subject to any disclaimer, the term of this patent is extended or adjusted under 35 U.S.C. 154(b) by 80 days.

(21) Appl. No.: 17/527,666

(22) Filed: Nov. 16, 2021

(65) Prior Publication Data

US 2022/0175478 A1    Jun. 9, 2022

(30) Foreign Application Priority Data

Dec. 3, 2020   (JP) ................................. 2020-200851

(51) Int. Cl.
*A61B 1/00*   (2006.01)
*A61B 34/35*   (2016.01)
(Continued)

(52) U.S. Cl.
CPC .......... *A61B 34/35* (2016.02); *A61B 1/00009* (2013.01); *A61B 1/00045* (2013.01);
(Continued)

(58) Field of Classification Search
CPC ......... A61B 34/76; A61B 34/35; A61B 34/70; A61B 1/00045; A61B 1/00009;
(Continued)

(56) References Cited

U.S. PATENT DOCUMENTS 7,660,623 B2   2/2010   Hunter et al.
7,789,875 B2   9/2010   Brock et al.
(Continued)

FOREIGN PATENT DOCUMENTS

GB    2560390 A    9/2018
GB    2560390 A8    10/2018
(Continued)

*Primary Examiner* — Anh Tuan T Nguyen
*Assistant Examiner* — Sung Ham
(74) *Attorney, Agent, or Firm* — METROLEX IP LAW GROUP, PLLC

(57) ABSTRACT

A robotic surgical system according to one or more embodiments may include: an endoscope; a manipulator configured to support a surgical instrument; a remote control apparatus including a display device and an operation handle configured to operate the surgical instrument; and a control device configured to display, on the display device, a graphical user interface on an image captured by the endoscope. The graphical user interface includes: a first area that displays a first graphical display indicating a movable range of the manipulator and an operable range of the operation handle in the movable range of the manipulator; and a second area that displays a second graphical display indicating a required operation of the operation handle to return the operation handle to an inside of the operable range of the operation handle and/or to return the manipulator to an inside of the movable range of the manipulator.

17 Claims, 19 Drawing Sheets

(51) Int. Cl.
  *A61B 34/00* (2016.01)
  *A61B 34/30* (2016.01)
(52) U.S. Cl.
  CPC .............. *A61B 34/25* (2016.02); *A61B 34/70* (2016.02); *A61B 2034/301* (2016.02)
(58) Field of Classification Search
  CPC .............. A61B 34/25; A61B 2090/373; A61B 2034/2059; A61B 2017/00973; A61B 2034/742; A61B 2034/301
  See application file for complete search history.

(56) References Cited

U.S. PATENT DOCUMENTS

| | | | |
|---|---|---|---|
| 8,052,636 B2 | 11/2011 | Moll et al. | |
| 8,315,720 B2 | 11/2012 | Mohr et al. | |
| 8,473,031 B2 | 6/2013 | Nixon et al. | |
| 8,583,274 B2 | 11/2013 | Mohr et al. | |
| 8,594,841 B2 | 11/2013 | Zhao et al. | |
| 8,892,224 B2 | 11/2014 | Mohr et al. | |
| 9,089,256 B2 | 7/2015 | Tognaccini et al. | |
| 9,218,053 B2 | 12/2015 | Komuro et al. | |
| 9,603,665 B2 | 3/2017 | Bowling et al. | |
| 9,707,043 B2 | 7/2017 | Bozung | |
| 9,788,909 B2 | 10/2017 | Larkin et al. | |
| 10,008,017 B2 | 6/2018 | Itkowitz et al. | |
| 10,123,846 B2 | 11/2018 | Suresh et al. | |
| 10,537,398 B2 | 1/2020 | Yorimoto et al. | |
| 10,568,701 B2 | 2/2020 | Swayze et al. | |
| 2017/0360519 A1* | 12/2017 | Yorimoto | B25J 13/02 |
| 2018/0098817 A1* | 4/2018 | Nichogi | A61B 34/37 |
| 2018/0353245 A1* | 12/2018 | Mccloud | A61B 34/30 |
| 2019/0239972 A1* | 8/2019 | Chassot | A61B 34/74 |
| 2019/0314097 A1* | 10/2019 | Diolaiti | A61B 34/70 |
| 2020/0038125 A1* | 2/2020 | Farlow | A61B 34/30 |
| 2020/0039066 A1* | 2/2020 | Oguri | B25J 9/1689 |
| 2020/0093551 A1 | 3/2020 | Ishihara et al. | |
| 2020/0205916 A1 | 7/2020 | Ishihara et al. | |
| 2020/0222138 A1* | 7/2020 | Diolaiti | A61B 34/76 |
| 2021/0145526 A1* | 5/2021 | Robinson | G05B 19/042 |
| 2021/0369328 A1* | 12/2021 | Joseph | A61B 34/25 |

FOREIGN PATENT DOCUMENTS

| | | | |
|---|---|---|---|
| JP | 2001-104333 A | | 4/2001 |
| JP | 2002-253574 A | | 9/2002 |
| JP | 2002253574 A | * | 9/2002 |
| JP | 2019-500945 A | | 1/2019 |
| JP | 2020-96923 A | | 6/2020 |

\* cited by examiner

TCP2
TCP

First Graphical Display GR1

Second Graphical Display GR2

FIG. 22

CASE A

| HC (Operation Handle) | | Arm | | 1st Graphical Display GR1 |
|---|---|---|---|---|
| Counterclockwise Direction | Clockwise Direction | State | | |
| | | Left | Right | |
| Margin | No Margin | Margin | Margin | ▽—MK  G8 / L10  L1 |

| Purpose | 2nd Graphical Display GR2 (Icon to Instruct Required Operation) |
|---|---|
| To extend the operable range of the operation handle to the right | a3, a2, a1, 360°  G9 |

| Operation | 1st Graphical Display GR1 After Operation |
|---|---|
| Depress the clutch pedal and rotate the operation handle to the left (in the counterclockwise direction) by 360 degrees | ▽  G8 |

FIG. 23

CASE B

| HC (Operation Handle) | | Arm | | 1st Graphical Display GR1 |
|---|---|---|---|---|
| Counterclockwise Direction | Clockwise Direction | State | | |
| | | Left | Right | |
| No Margin | Margin | Margin | Margin | MK ▽ G8 / L1 L10 |

| Purpose | 2nd Graphical Display GR2 (Icon to Instruct Required Operation) |
|---|---|
| To extend the operable range of the operation handle to the left | a2, a3, 360°, a1 — G9 |

| Operation | 1st Graphical Display GR1 After Operation |
|---|---|
| Depress the clutch pedal and rotate the operation handle to the right (in the clockwise direction) by 360 degrees | ▽ G8 |

FIG. 24

CASE C

| HC (Operation Handle) | | Arm | | 1st Graphical Display GR1 |
|---|---|---|---|---|
| Counterclockwise Direction | Clockwise Direction | State | | |
| | | Left | Right | |
| No Margin | Margin | No Margin | Margin | ▽—MK  G8<br>L1    L10 |

| Purpose | 2nd Graphical Display GR2<br>(Icon to Instruct Required Operation) |
|---|---|
| To move the operation handle to the position where the operation handle is movable in the left and right directions | a2  G9<br>360°  a1 |

| Operation | 1st Graphical Display GR1 After Operation |
|---|---|
| Rotate the operation handle to the right (in the clockwise direction) by 360 degrees | ▽  G8 |

FIG. 25

CASE D

| HC (Operation Handle) | | Arm | | 1st Graphical Display GR1 |
|---|---|---|---|---|
| Counterclockwise Direction | Clockwise Direction | State | | |
| | | Left | Right | |
| Margin | No Margin | Margin | No Margin | 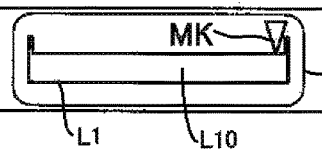 |

| Purpose | 2nd Graphical Display GR2 (Icon to Instruct Required Operation) |
|---|---|
| To move the operation handle to the position where the operation handle is movable in the left and right directions | 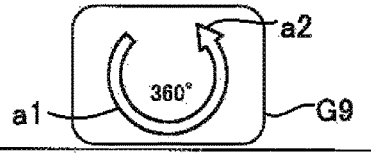 |

| Operation | 1st Graphical Display GR1 After Operation |
|---|---|
| Rotate the operation handle to the left (in the counterclockwise direction) by 360 degrees | 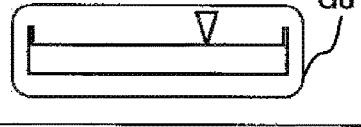 |

FIG. 27

CASE E

| HC (Operation Handle) | | Arm | | 1st Graphical Display GR1 |
|---|---|---|---|---|
| Counterclockwise Direction | Clockwise Direction | State | | |
| | | Left | Right | |
| Margin | No Margin | Margin | Margin | ▽―MK  G8 / L10  L1 |

| Purpose | 2nd Graphical Display GR2 (Icon to Instruct Required Operation) |
|---|---|
| To extend the operable range of the operation handle to the right | a3, a2, a1, 360°, G9 |

| Operation 1 | 1st Graphical Display GR1 After Operation 1 |
|---|---|
| Depress the clutch pedal and rotate the operation handle to the left (in the counterclockwise direction) by 360 degrees | ▽―MK  G8 / L10  L1 |

| | 2nd Graphical Display GR2 (Icon to Instruct Required Operation) |
|---|---|
| | a3, a1, 180°, a2, G9 |

| Operation 2 | 1st Graphical Display GR1 After Operation 2 |
|---|---|
| Depress the clutch pedal and rotate the operation handle to the left (in the counterclockwise direction) by 180 degrees | ▽  G8 |

FIG. 28

CASE F

| HC (Operation Handle) | | Arm | | 1st Graphical Display GR1 |
|---|---|---|---|---|
| Counterclockwise Direction | Clockwise Direction | State | | |
| | | Left | Right | |
| Margin | Margin | No Margin | Margin | 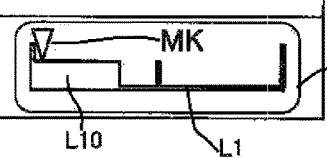 |

| Purpose | 2nd Graphical Display GR2 (Icon to Instruct Required Operation) |
|---|---|
| To extend the operable range of the operation handle to the right<br>To move the operation handle to the position where the operation handle is movable in the left and right directions | 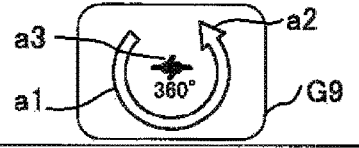 |

| Operation 1 | 1st Graphical Display GR1 After Operation 1 |
|---|---|
| To depress the clutch pedal and rotate the operation handle to the left (in the counterclockwise direction) by 360 degrees | 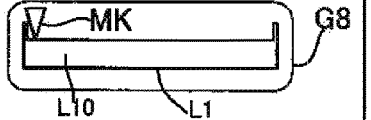 |
| | 2nd Graphical Display GR2 (Icon to Instruct Required Operation)<br>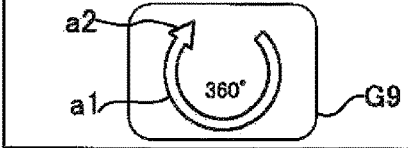 |

| Operation 2 | 1st Graphical Display GR1 After Operation 2 |
|---|---|
| Rotate the operation handle to the right (in the clockwise direction) by 360 degrees | 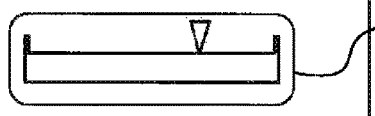 |

ROBOTIC SURGICAL SYSTEM AND DISPLAY METHOD

CROSS REFERENCE TO RELATED APPLICATIONS

This application claims priority based on 35 USC 119 from prior Japanese Patent Application No. 2020-200851 filed on Dec. 3, 2020, entitled "ROBOTIC SURGICAL SYSTEM AND DISPLAY METHOD", the entire contents of which are incorporated herein by reference.

BACKGROUND

The disclosure may relate to a robotic surgical system and a display method, and more particularly to a robotic surgical system and a display method in which a graphical user interface is displayed on an image captured by an endoscope.

In a related art, there is known a robotic surgical system that superimposes and displays a graphical user interface on an image captured by an endoscope (see, for example, Patent Document 1: JP2019-500945).

Patent Document 1 discloses a robotic surgical system that includes a device including an end effector, a hand controller (or an operation handle) for operating the end effector, and a display device. In this robotic surgical system, a graphic depiction (a graphical user interface) is displayed in the display device, wherein the graphical depiction includes: a surgical workspace (an image captured by the endoscope); an end-effector movable range including a boundary indicating the limit of movement of the end-effector in the surgical workspace; and a two-dimensional projection of the current spatial position of the end-effector.

In the robotic surgical system disclosed in Patent Document 1, the hand controller that operates the end effector may reach the end of the operable range of the hand controller. In this case, it may be necessary to return the hand controller to the inside of the operable range of the hand controller by operating the hand controller after disconnecting the connection between the hand controller and the end effector. Also, in the robotic surgical system, the end effector may reach the end of the movable range of the end effector (the movement limit of the end effector) during the operation. In this case, it may be necessary to return the end effector to the inside of the movable range of the end effector by operating the hand controller.
Patent Document 1: JP2019-500945

SUMMARY

However, in Patent Document 1, when the hand controller reaches the end of the operable range of the hand controller or when the end effector (manipulator) reaches the movement limit of the end effector (the end of the movable range of the end effector), it may be difficult for the operator to recognize how to operate the hand controller (operation handle) to return the hand controller to the inside of the operable range thereof or return the end effector to the inside of the movable range thereof.

An object of one or more embodiments of the disclosure is to provide a robotic surgical system and a display method that allow an operator to easily recognize an operation of an operation handle for returning (repositioning) the operation handle to an inside of an operable range of the operation handle and/or for returning (repositioning) a manipulator to an inside of a movable range of the manipulator.

A first aspect of the disclosure may be a robotic surgical system that may include: an endoscope configured to capture an image of a surgical site; a manipulator configured to support a surgical instrument; a display device configured to display thereon the image captured by the endoscope; a remote control apparatus including an operation handle to operate the surgical instrument; and a control device configured to generate a graphical user interface and display, on the display device, the graphical user interface on the image captured by the endoscope in an overlapped manner. The graphical user interface may include a first area and a second area different from the first area, wherein the first area displays a first graphical display indicating a movable range of the manipulator and an operable range of the operation handle in the movable range of the manipulator, and the second area displays a second graphical display indicating a required operation of the operation handle to return the operation handle to an inside of the operable range of the operation handle and/or to return the manipulator to an inside of the movable range of the manipulator.

In the robotic surgical system according to the first aspect, the graphical user interface Includes the second area that is different from the first area and that displays the second graphical display indicating the required operation of the operation handle required to return the operation handle to the inside of the operable range of the operation handle and/or to return the manipulator to the inside of the movable range of the manipulator. Here, in the robotic surgical system, the movement amount of the manipulator may be scaled so as to be smaller than the operation amount received by the operation handle. In this case, even if the manipulator is positioned within the movable range of the manipulator, the operation handle may be out of the operable range of the operation handle, and thus the operator may need to disconnect the operational connection between the operation handle and the manipulator and then return the operation handle to the inside of the operable range of the operation handle. Further, while repeating such an operation, the manipulator may reach the end of the movable range of the manipulator, and thus the operator may need to return the manipulator to the inside of the movable range of the manipulator. In view of this, the robotic surgical system according to the first aspect is configured as described above. Thus, the operator can recognize the required operation of the operation handle to return the operation handle to the inside of the operable range and/or to return the manipulator to the inside of the movable range of the manipulator, by visually checking the second area of the graphical user interface. As a result, the operator can easily recognize the required operation of the operation handle to return the operation handle to the inside of the operable range and/or to return the manipulator to the inside of the movable range of the manipulator.

Further, according the first aspect, the graphical user interface includes the first area that displays the first graphical display indicating the movable range of the manipulator and the operable range of the operation handle in the movable range of the manipulator. With this configuration, by visually checking the first area of the graphical user interface, the operator can easily recognize whether or not the operation handle is approaching the end of the operable range of the operation handle, and whether or not the manipulator is approaching the end of the movable range of the manipulator.

A second aspect of the disclosure may be a display method that may include: acquiring an image that is captured by an endoscope configured to capture an image of a surgical site, generating a graphical user interface and displaying, on a display device, the graphical user interface on the image captured by the endoscope in an overlapped manner. The displaying of the graphical user interface may include: displaying, in a first area in the graphical user interface, a first graphical display indicating a movable range of an manipulator configured to support a surgical instrument and an operable range of an operation handle configured to operate the manipulator in the movable range of the manipulator; and displaying, in a second area different from the first area in the graphical user interface, a second graphical display indicating a required operation of the operation handle to return the operation handle to an inside of the operable range of the operation handle and/or to return the manipulator to an inside of the movable range of the manipulator.

As described above, according to the second aspect, the displaying of the graphical user interface includes displaying, in the second area different from the first area in the graphical user interface, the second graphical display indicating the required operation of the operation handle to return the operation handle to the inside of the operable range of the operation handle and/or to return the manipulator to the inside of the movable range of the manipulator. Here, in such a robotic surgical system, a movement amount of the manipulator may be scaled so as to be smaller than the operation amount received by the operation handle. In this case, even if the manipulator is positioned within the movable range of the manipulator, the operation handle may be out of the operable range of the operation handle, and thus the operator may need to disconnect the operational connection between the operation handle and the manipulator and then return the operation handle to the inside of the operable range of the operation handle. Further, while repeating such an operation, the manipulator may reach the end of the movable range of the manipulator, and thus the operator may need to return the manipulator to the inside of the movable range of the manipulator. In view of this, the display method according to the second aspect is configured as described above. Thus, the operator can recognize the required operation of the operation handle to return the operation handle to the inside of the operable range and/or return the manipulator to the inside of the movable range of the manipulator, by visually checking the second area of the graphical user interface. As a result, it is possible to provide a display method that allows the operator to easily recognize the operation of the operation handle required to return the operation handle to the inside of the operable range and/or to return the manipulator to the inside of the movable range of the manipulator.

In addition, the displaying of the graphical user interface includes displaying, in the first area in the graphical user interface, the first graphical display indicating the movable range of the manipulator configured to support the surgical instrument and the operable range of the operation handle to operate the manipulator in the movable range of the manipulator. As a result, it is possible to provide a display method that allows the operator to easily recognize whether or not the operation handle is approaching the end of the operable range of the operation handle and whether or not the manipulator is approaching the end of the movable range of the manipulator, by visually checking the first area of the graphical user interface.

According to the disclosure, an operator can easily recognize an operation of an operation handle to return the operation handle to an inside of an operable range of the operation handle and/or to return a manipulator to an inside of a movable range of the manipulator.

BRIEF DESCRIPTION OF DRAWINGS

FIG. 22 is a diagram (Case A) for explaining an operation of the operation handle;
FIG. 23 is a diagram (Case B) for explaining an operation of the operation handle;
FIG. 24 is a diagram (Case C) for explaining an operation of the operation handle;
FIG. 25 is a diagram (Case D) for explaining an operation of the operation handle;
FIG. 27 is a diagram (Case E) for explaining an operation of the operation handle according to a second embodiment;
and
FIG. 28 is a diagram (Case F) for explaining an operation of the operation handle according to a second embodiment.

DETAILED DESCRIPTION

Figure 1:
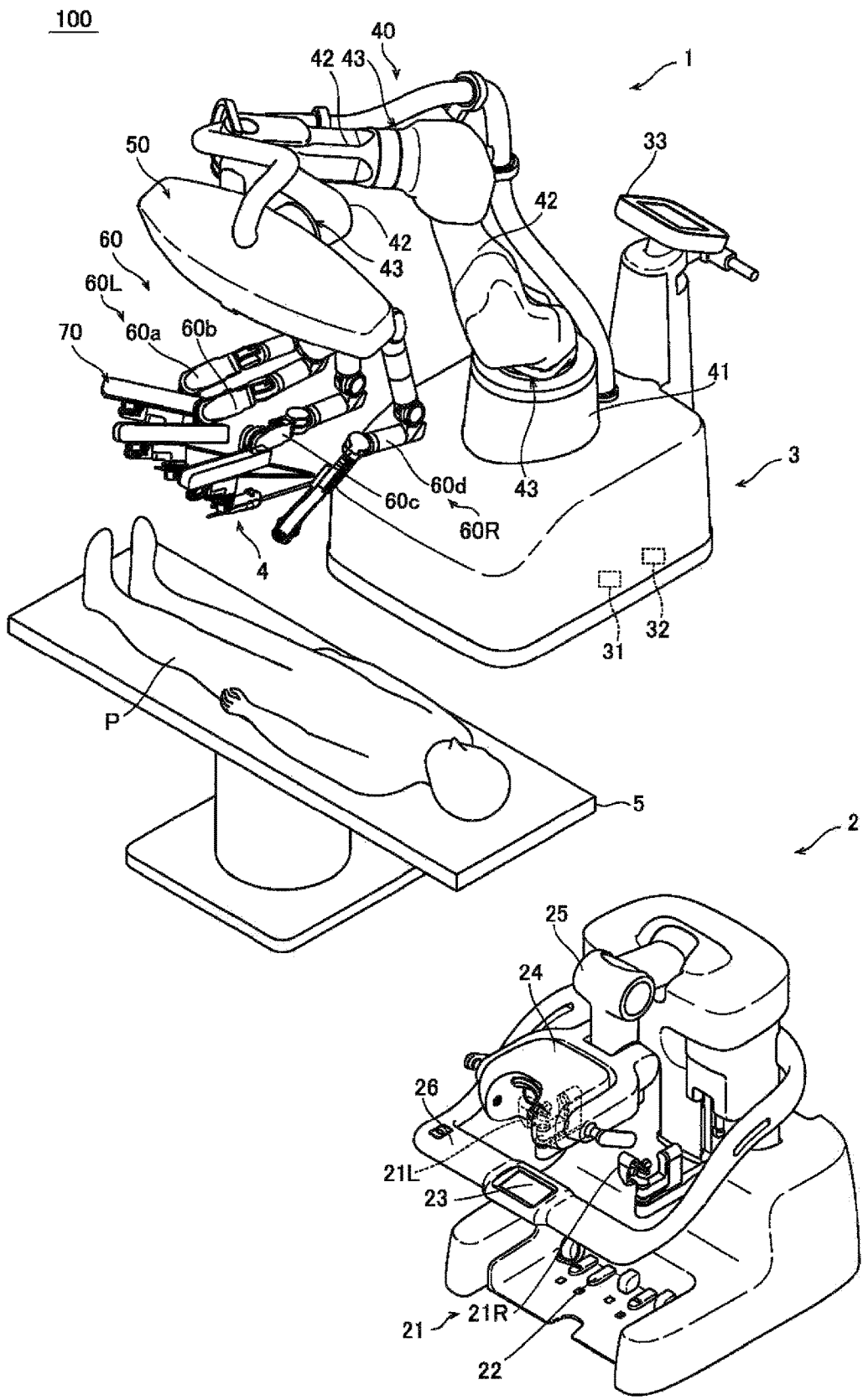
FIG. 1 is a diagram illustrating a view of a configuration of a surgical operation system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment

A configuration of a surgical operation system 100 according to a first embodiment is described with reference to FIGS. 1 to 26. The surgical operation system 100 includes a medical manipulator 1 serving as a patient-side apparatus and a remote control apparatus 2 serving as an operator-side apparatus to operate the medical manipulator 1. The medical manipulator 1 is provided with a medical trolley 3 and is thus configured to be movable. The remote control apparatus 2 is provided at a location away from the medical manipulator 1. The medical manipulator 1 is configured to be remotely operated by the remote control apparatus 2. An operator (such as a doctor) inputs to the remote control apparatus 2 an instruction that causes the medical manipulator 1 to perform a desired operation. The remote control apparatus 2 transmits the input instruction to the medical manipulator 1. The medical manipulator 1 operates in response to the received instruction. The medical manipulator 1 is disposed in a surgery room, as a sterile field, which is sterilized. The surgical operation system 100 is an example of a "robotic surgical system".

The remote control apparatus 2 is disposed inside the surgery room or outside the surgery room, for example. The remote control apparatus 2 includes operation handles 21, foot pedals 22, a touch panel 23, a monitor 24, a support arm 25, and a support bar 26. The operation handles 21 are hand controllers (HC) provided for the operator (such as a doctor) to input instructions. Note that the monitor 24 is an example of a "display device".

The operation handles 21 are configured to operate the medical instruments 4. Specifically, the operation handles 21 receive an amount of movement inputted by the operator O to operate the medical instruments 4. The operation handles 21 include an operation handle 21L, which is arranged on the left side of the operator (such as a doctor) and is to be operated by the left hand of the operator O, and an operation handle 21R, which is arranged on the right side of the operator and is to be operated by the right hand of the operator O.

Figure 3:
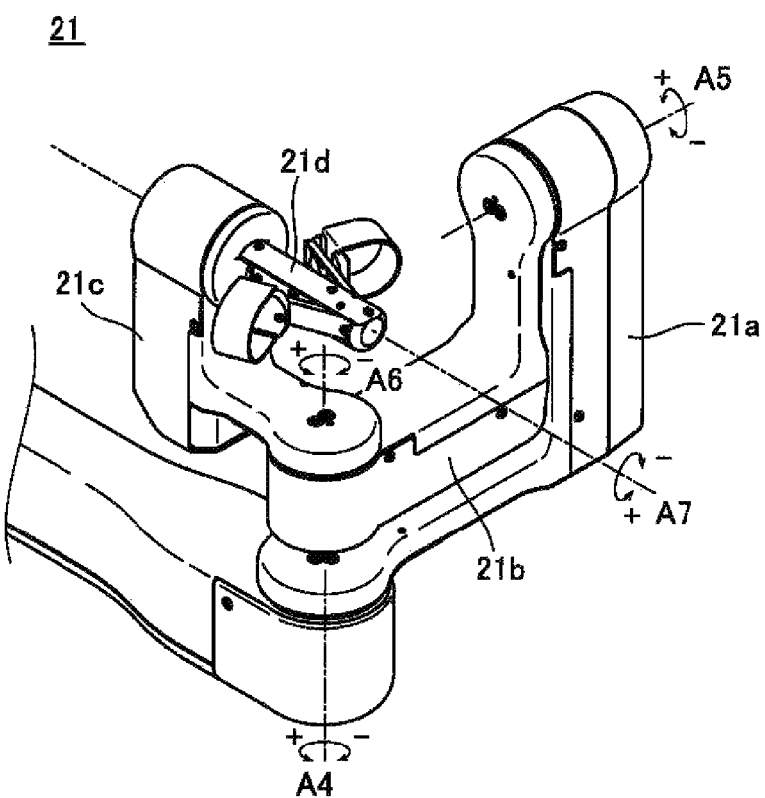
FIG. 3 is a diagram illustrating a view of a configuration of an operation handle according to a first embodiment.

As illustrated in FIG. 3, each of the operation handles 21 includes a link portion 21a, a link portion 21b, a link portion 21c, and a link portion 21d that is to be operated by the operator (such as a doctor). The link portion 21a is rotatable about an axis (joint) A4. By rotating the link portion 21a around the axis A4, the arm portion 61 described later rotates about an axis (joint) JT4. The link portion 21b is rotatable about an axis (joint) A5 with respect to the link portion 21a. By rotating the link portion 21b around the axis A5, the arm portion 61 described later rotates about an axis (joint) JT5. The link portion 21c is rotatable about an axis (joint) A6 with respect to the link portion 21b. By rotating the link portion 21c around the axis A6, the arm portion 61 rotates about an axis (joint) JT6. The link portion 21d is rotatable about an axis (joint) A7 with respect to the link portion 21c. By rotating the link portion 21d around the axis A7, the arm portion 61 rotates about an axis (joint) JT7. The medical instrument 4 is an example of a "surgical instrument", a "first surgical instrument", or a "second surgical instrument". The operation handle 21L and the operation handle 21R are examples of a "first operation handle" and a "second operation handle", respectively.

Further, a movement amount of the arm 60 (medical instrument 4) is scaled (changed) with respect to the operation amount received by the operation handle 21. For example, when the movement scaling ratio is set to ½, the medical instrument 4 moves ½ of the movement distance of the operation handle 21. This allows for precise fine surgery. The arm 60 is an example of a "manipulator".

Figure 4:
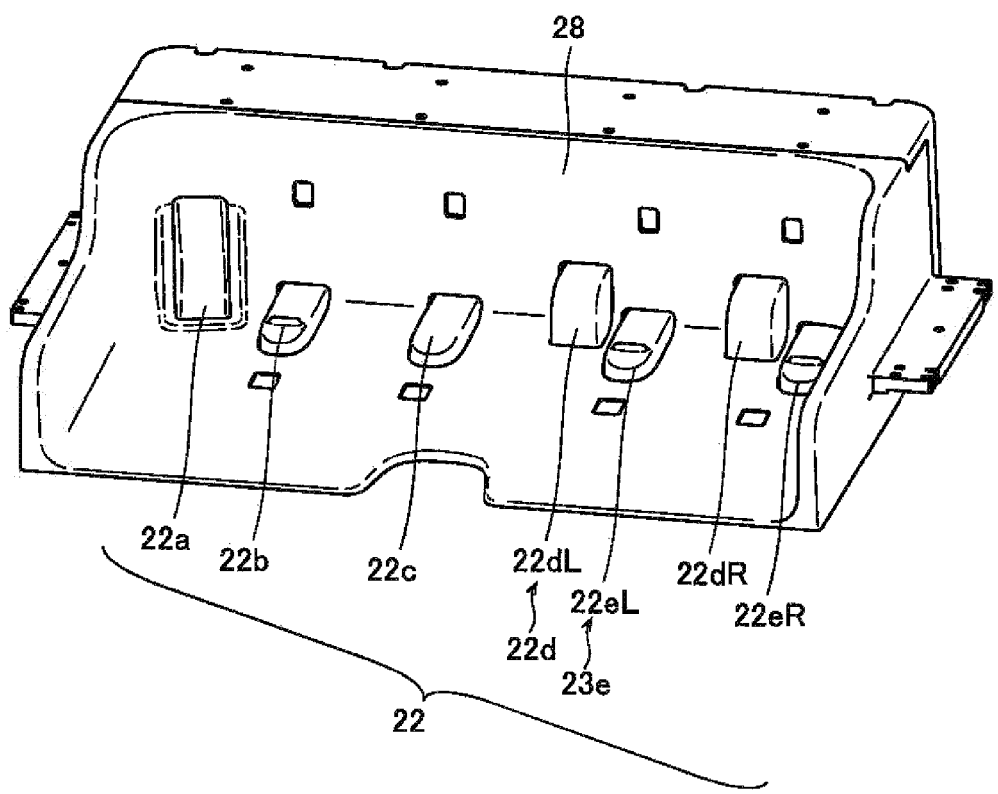
FIG. 4 is a diagram illustrating a view of foot pedals according to a first embodiment.

As illustrated in FIG. 4, the plural foot pedals 22 are provided to execute functions of the medical instrument 4. The plural foot pedals 22 are arranged on a base 28. The foot pedals 22 include a switch pedal 22a, a clutch pedal 22b, a camera pedal 22c, cutting pedals 22d, and coagulation pedals 22e. The switch pedal 22a, the clutch pedal 22b, the camera pedal 22c, the cutting pedals 22d, and the coagulation pedals 22e are operated by the foot of the operator. The cutting pedals 22d includes a cutting pedal 22dR for the right arm 60 and a cutting pedal 22dL for the left arm 60. The coagulation pedals 22e include a coagulation pedal 22eR for the right arm 60 and a coagulation pedal 22eL for the left arm 60. The clutch pedal 22b is an example of an "input device".

The switch pedal 22a is configured to select one of the arms 60 that is to be operated by the operation handles 21. In a first embodiment, the clutch pedal 22b is configured to perform a clutch operation that temporarily disconnects the operational connection between the arm 60 and the operation handle 21. While the clutch pedal 22b is depressed by the operator, the operation by the operation handle 21 is not transmitted to the arm 60. Further, while the camera pedal 22c is depressed by the operator, the operation handles 21 (operation handle 21R, operation handle 21L) can operate the endoscope 6 (the arm 60 to which the endoscope 6 is attached). While the cutting pedal 22d (coagulation pedal 22e) is depressed by the operator, an electrosurgical device (not illustrated) is activated.

As illustrated in FIG. 1, the monitor 24 is a display device of a scope type configured to display an image gr (see FIG. 13) captured by the endoscope 6. The support arm 25 supports the monitor 24 in such a manner that the height of the monitor 24 is adjusted to the height of the face of the operator (such as a doctor). The touch panel 23 is disposed on the support bar 26. When a sensor(s) (not illustrated) provided in the vicinity of the monitor 24 detect(s) the head of the operator, the medical manipulator 1 is allowed to be operated by the remote control apparatus 2. The operator operates the operation handles 21 and the foot pedals 22, while viewing the surgical site (or affected area) displayed on the monitor 24. With this, the instruction is inputted to the remote control apparatus 2. The instruction that is inputted to the remote control apparatus 2 is transmitted to the medical manipulator 1.

The medical trolley 3 is provided with a control unit 31 that controls the operation of the medical manipulator 1 and a storage 32 that stores therein programs for controlling the operation of the medical manipulator 1. Based on the instruction inputted to the remote control apparatus 2, the control unit 31 of the medical trolley 3 controls the operation of the medical manipulator 1.

Further, the medical trolley 3 is provided with an input device 33. The input device 33 is configured to accept operations to move or change posture of a positioner 40, an arm base 50, and the arms 60, mainly to prepare for surgery before the surgery.

Figure 2:
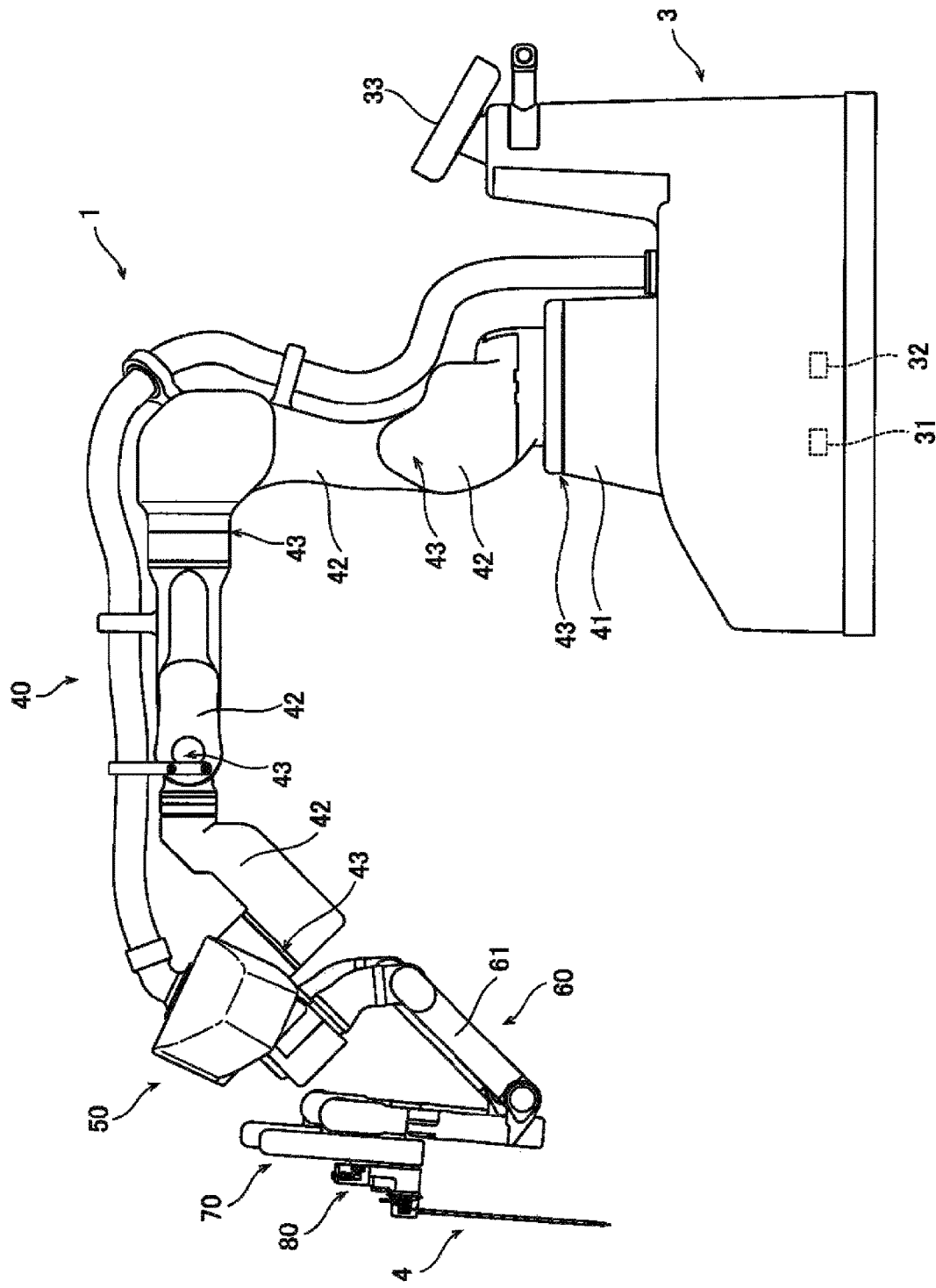
FIG. 2 is a diagram illustrating a view of a configuration of a medical manipulator according to a first embodiment.

As illustrated in FIGS. 1 and 2, the medical manipulator 1 is disposed in the surgery room. The medical manipulator 1 includes the medical trolley 3, the positioner 40, the arm base 50, and the arms 60. The arm base 50 is attached to a distal end of the positioner 40. The arm base 50 is in a relatively long rod shape (elongate shape). Base portions (proximal end portions) of the arms 60 are attached to the arm base 50. Each of the arms 60 is configured such that the arm 60 is able to take a folded posture (storage posture). The arm base 50 and the arms 60 are used with being covered with a sterile drape (not illustrated). The arm 60 supports the medical instrument 4. The arm 60 is an example of a "manipulator". The medical instrument 4 is an example of a "surgical instrument".

The positioner 40 is configured as a 7-axis articulated robot. The positioner 40 is disposed on the medical trolley 3. The positioner 40 is configured to move the arm base 50. Specifically, the positioner 40 is configured to move the position of the arm base 50 three-dimensionally.

The positioner 40 includes a base portion 41 and link portions 42 connected to the base portion 41. The link portions 42 are connected to each other via joints 43.

As illustrated in FIG. 1, to the distal end of each of the arms 60, the medical instrument 4 is attached. The medical instruments 4 include, for example, an instrument that is replaceable, an endoscope 6 (see FIG. 8) configured to capture an image gr of a surgical site, and the like.

Figure 5:
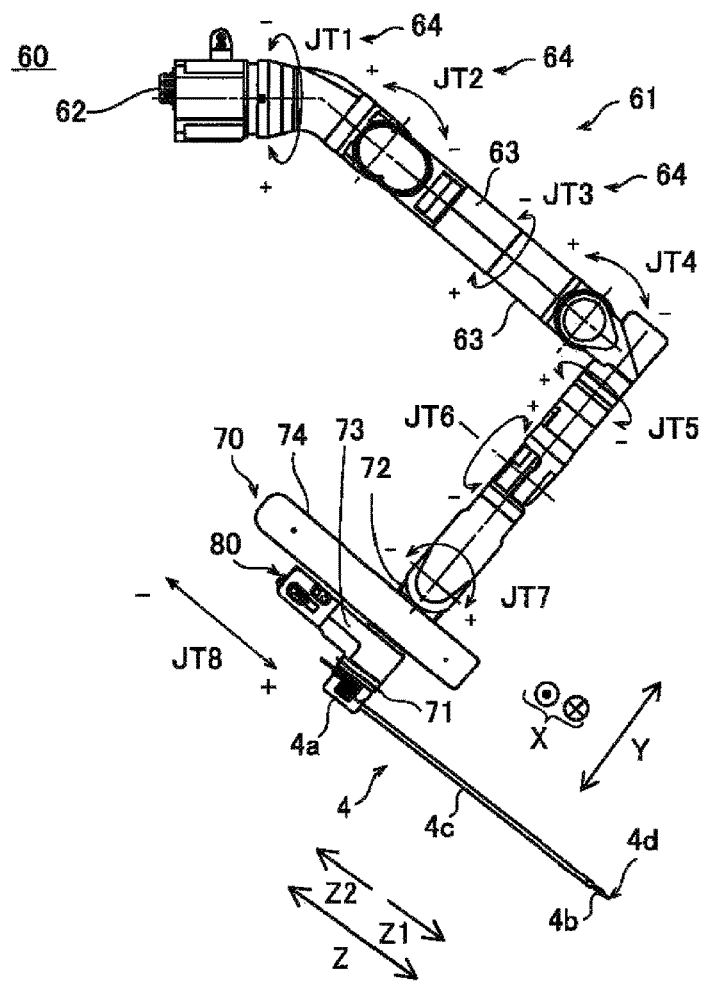
FIG. 5 is a diagram illustrating a view of a configuration of an arm of the medical manipulator according to a first embodiment.

As illustrated in FIG. 5, the instrument is provided with a driven unit 4a, which is driven by servomotors M2 provided in a holder 71 of the arm 60. To the distal end of the instrument, forceps 4b as an end effector is provided.

Figure 6:
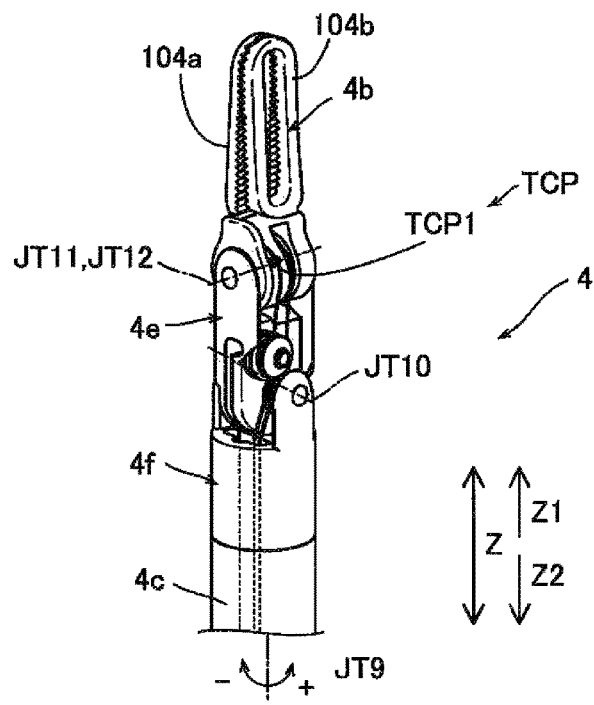
FIG. 6 is a diagram illustrating a view of forceps.

As illustrated in FIG. 6, the instrument includes: a first support 4e having a distal end portion thereof that rotatably supports proximal end portions of end effector members 104a and 104b about an axis (joint) JT11; a second support 4f having a distal end portion thereof that rotatably supports a proximal end portion of the first support 4e about an axis (joint) JT10; and a shaft 4c connected a proximal end portion of the second support 4f. The driven unit 4a, the shaft 4c, the second support 4f, the first support 4e, and the forceps 4b are arranged along the Z direction. The axis JT11 is orthogonal to a direction (Z direction) in which the shaft 4c extends. The axis JT10 is provided away from the axis JT11 in the direction in which the shaft 4c extends, and is orthogonal to the axis JT11 and orthogonal to the direction in which the shaft 4c extends.

The forceps 4b is attached to the first support 4e so as to be rotatable about the axis JT11. The second support 4f rotatably supports the first support 4e about the axis JT10. In other words, the first support 4e is attached to the second support 4f so as to be rotatable about the axis JT10. A distal side (Z1 side) portion of the first support 4e has a U-shape. A tool center point (TCP1, Clevis) is set at the center, along the axis JT11, of the U-shaped distal side portion of the first support 4e.

The medical instrument 4 (forceps 4b) includes an axis (joint) JT9 as a rotation axis of the shaft 4c (extending along the direction in which the shaft 4c extends) and an axis (joint) JT12 about which the forceps 4b opens and closes. Note that the plural (for example, four) servomotors M2 are provided in the holder 71 of the arm 60, and rotors (rotation members) in the driven unit 4a are driven by the plural servomotors M2. As a result, the medical instrument 4 is driven about the axes J9 to J12.

Figure 8:
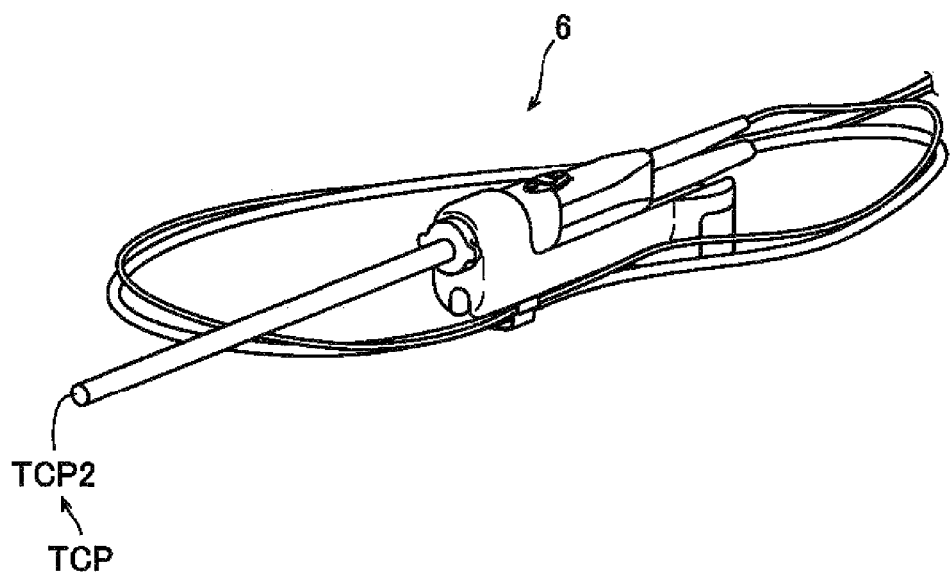
FIG. 8 is a diagram illustrating a view of an endoscope.
Figure 9:
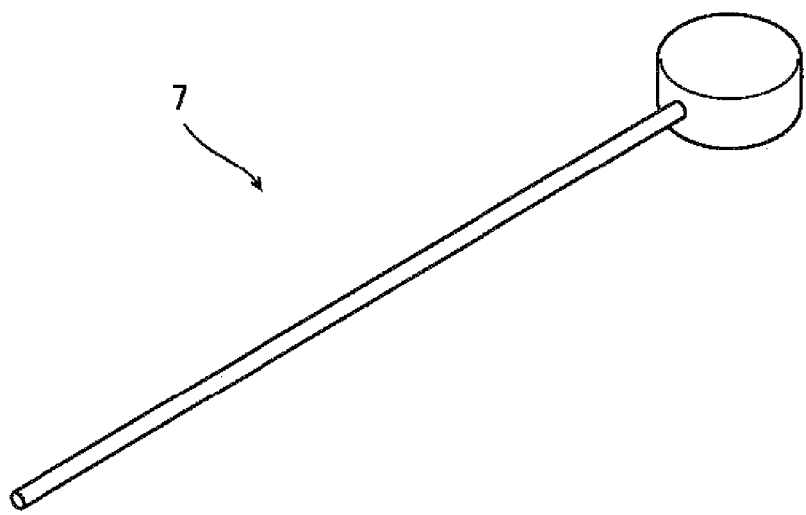
FIG. 9 is a diagram illustrating a view of a pivot position setting device.

As illustrated in FIG. 8, a tool center point TCP2 of the endoscope 6 is set at the distal end of the endoscope 6.

Next, a configuration of the arm 60 is described in detail. As illustrated in FIG. 5, the arm 60 includes an arm portion 61 (the base portion 62, the link portions 63, the joint portions 64) and a translation movement mechanism 70 provided at the distal end portion of the arm portion 61. The arm 60 is configured such that the distal end portion thereof is three-dimensionally movable with respect to the proximal side (the arm base 50) of the arm 60. The arm portion 61 is configured as a 7-axis articulated robot arm. The plural arms 60 have the same configuration.

Figure 12:
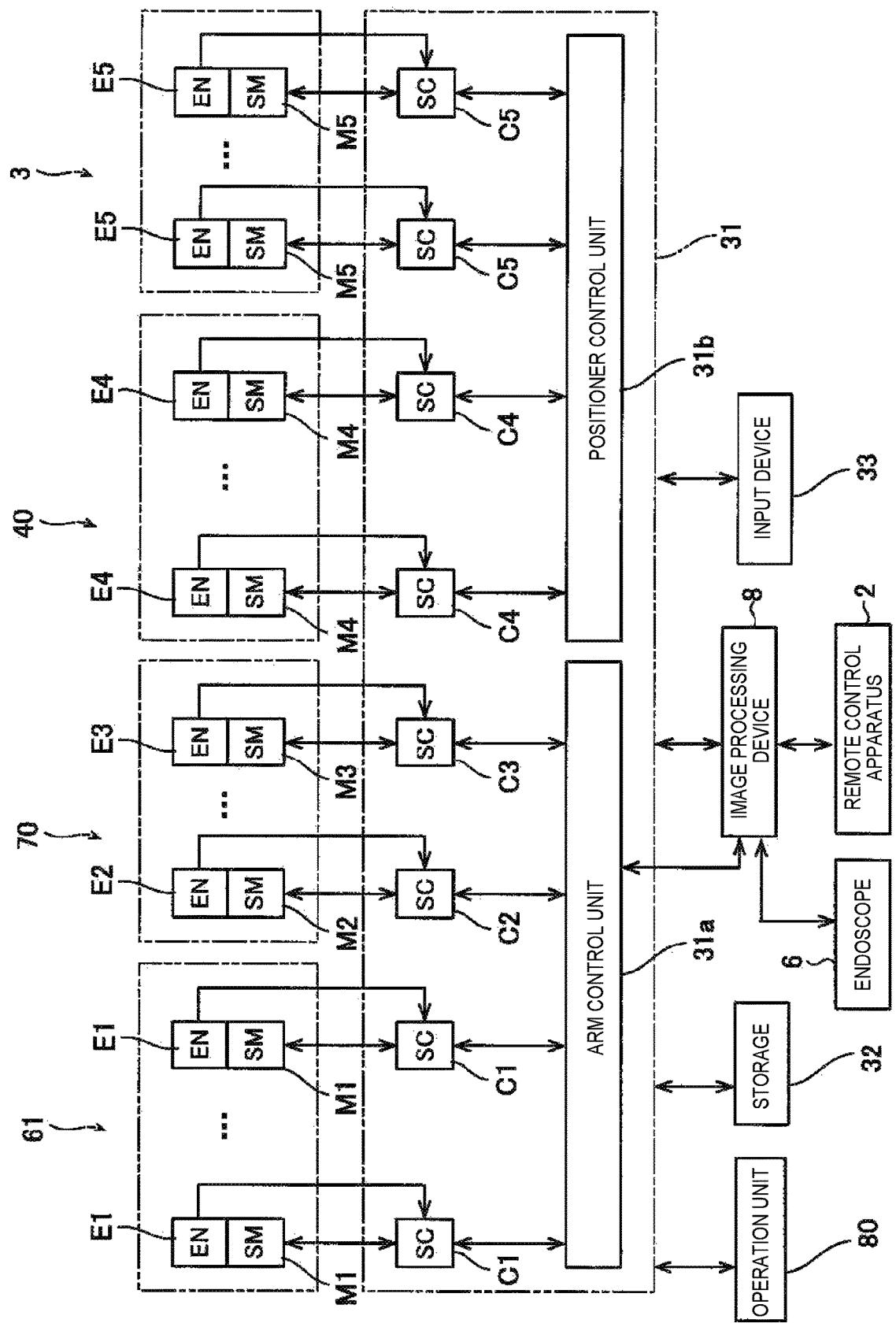
FIG. 12 is a block diagram illustrating a configuration of a control unit of the medical manipulator according to a first embodiment.
Figure 13:
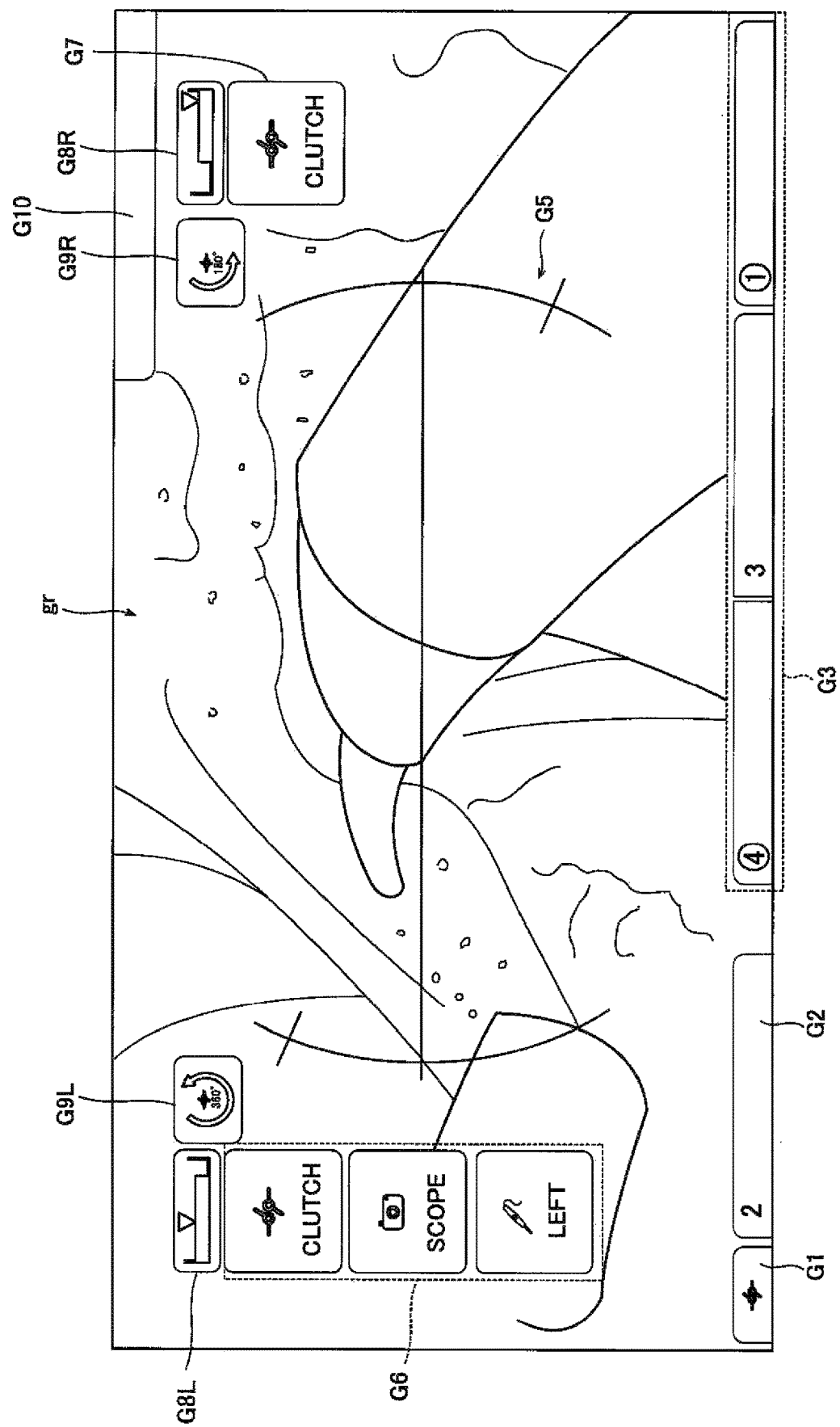
FIG. 13 is a diagram illustrating an image captured by the endoscope and a graphical user interface.

As illustrated in FIG. 5, the arm 60 includes the axis (joints) JT1 to JT7 as rotation axes and an axis (joint) JT8 as a linear motion axis. The axes JT1 to JT7 correspond to the rotation axes of the joint portions 64 of the arm portion 61. The axis JT7 corresponds to the proximal end side link portion 72 of the translational movement mechanism 70. An axis (joint) JT8 is an axis for moving the distal end side link portion 73 of the translational movement mechanism 70 relative to the proximal end side link portion 72 along the Z direction. That is, the servomotors M1 illustrated in FIG. 12 are provided to correspond to the joints JT1 to JT7 of the arm 60. The servomotor M3 is provided to correspond to the joint JT8.

The translation movement mechanism 70 is provided on a side of the distal end of the arm portion 61. The medical instrument 4 is attached to the translation movement mechanism 70. The translation movement mechanism 70 translationally moves the medical instrument 4 in the insertion direction of the medical instrument 4 into a patient P. The translation movement mechanism 70 is configured to translationally move the medical instrument 4 relative to the arm portion 61. Specifically, the translation movement mechanism 70 is provided with the holder 71 configured to hold the medical instrument 4. The holder 71 accommodates therein the servo-motors M2 (see FIG. 12).

Figure 7:
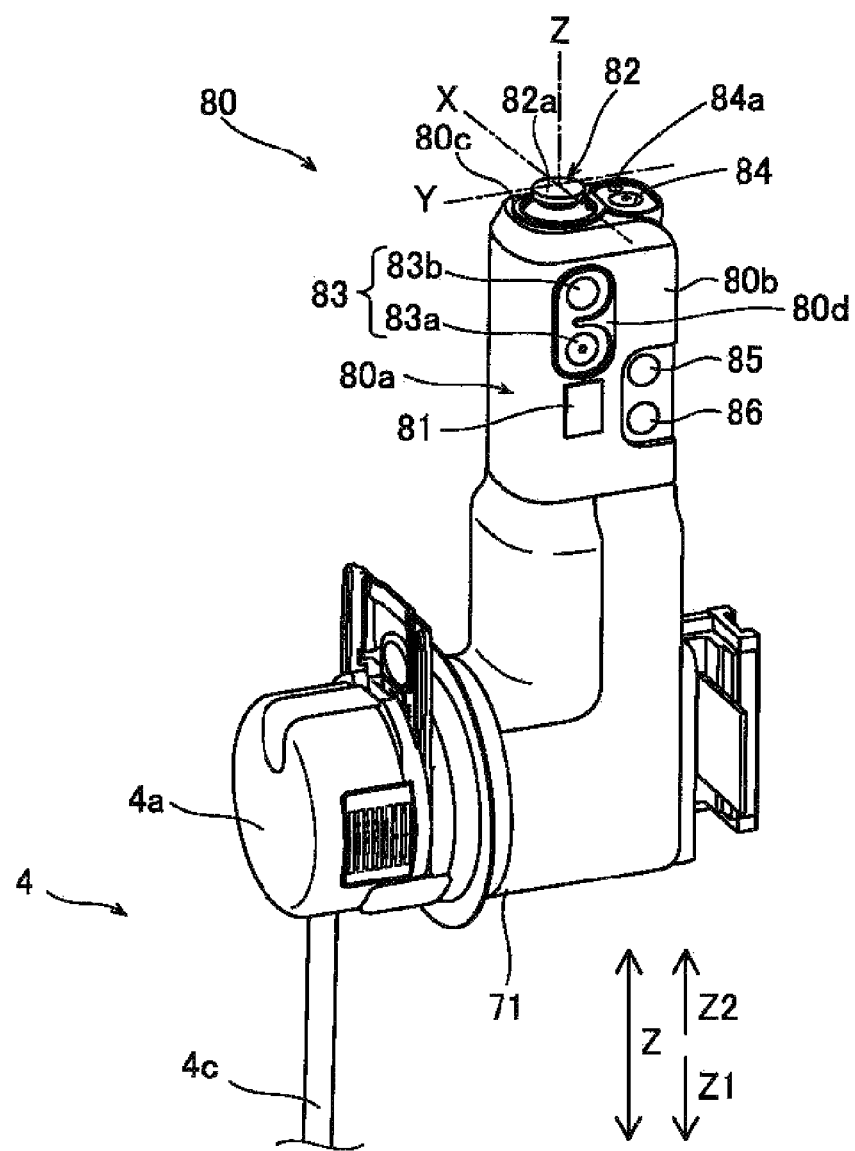
FIG. 7 is a diagram illustrating a perspective view of a configuration of an operation unit of the medical manipulator according to a first embodiment.

As illustrated in FIG. 7, the medical manipulator 1 includes an operation unit 80 which is attached to each of the arms 60 to operate the arm 60. The operation unit 80 includes an enable switch 81, a joystick 82, and a switch section 83. The enable switch 81 enables or disables the movements of the arm 60 in response to the joystick 82 and the switch section 83. While the enable switch 81 is being depressed by an operator (nurse, assistant, etc.) gripping the operation unit 80, the enable switch 81 enables the medical instrument 4 to move by the arm 60.

The switch section 83 includes: a switch 83a for moving the medical instrument 4 in the direction in which the medical instrument 4 is inserted into the patient P along the longitudinal direction of the medical instrument 4; and a switch 83b for moving the distal end 4d of the medical instrument 4 in the direction opposite to the direction in which the medical instrument 4 is inserted into the patient P. Both the switch 83a and the switch 83b are composed of push button switches.

As illustrated in FIG. 7, the operation unit 80 includes a pivot button 85 for setting a pivot position PP that serves as a fulcrum (see FIG. 11) for the movement of the medical instrument 4 attached to the arm 60. The pivot button 85 is provided on a surface 80b of the operation unit 80 so as to be adjacent to the enable switch 81. The pivot position PP is set, by pressing the pivot button 85 in a state where the distal end of the endoscope 6 (see FIG. 8) or the distal end of the pivot position teaching device 7 (FIG. 9) is located to a position corresponding to an insertion position of the trocar T inserted into the body surface S of the patient P. The set pivot position PP is stored in the storage 32. In the setting of the pivot position PP, the pivot position PP is set as one point (coordinate), but the setting of the pivot position PP does not set the direction of the medical instrument 4.

As illustrated in FIG. 1, the endoscope 6 is attached to one of the plural arms 60 (for example, the arm 60c), and the medical instruments 4 other than the endoscope 6 are attached to the other arms 60 (for example, the arms 60a, 60b, and 60d). Specifically, for surgery, the endoscope 6 is attached to one of the four arms 60, and the medical instruments 4 (forceps 4b, etc.) other than the endoscope 6 are attached to the other three arms 60. In the state where the endoscope 6 is attached to the arm 60, the pivot position PP for the endoscope 6 is set to the arm 60 to which the endoscope 6 is attached. Further, in the state where the pivot position setting device 7 is attached to the arm 60 to which the medical instrument 4 other than the endoscope 6 is attached, the pivot position PP for the medical instrument 4 is set to the arm 60 to which the medical instrument 4 other than the endoscope 6 is attached. The endoscope 6 is attached to one of two arms 60 (arms 60b and 60c) arranged in the central area among the four arms 60 arranged adjacent to each other. That is, the pivot position PP is individually set for each of the plurality of arms 60.

As illustrated in FIG. 7, the surface 80b of the operation unit 80 is provided with an adjustment button 86 for optimizing the position of the arm 60. After the pivot position PP is set to the arm 60 to which the endoscope 6 is attached, the positions of the other arms 60 (arm bases 50) are optimized by pressing the adjustment button 86.

As illustrated in FIG. 7, the operation unit 80 includes a mode switch button 84 for switching between a translational movement mode (see FIG. 10) to translationally move the medical instrument 4 attached to the arm 60 and a rotational movement mode (see FIG. 11) for rotationally move the medical instrument 4 attached to the arm 60. In the vicinity of the mode switch button 84, a mode indicator 84a is provided. The mode indicator 84a indicates the current mode. Specifically, when the mode indicator 84a is turned on (rotational movement mode) or turned off (translational movement mode), the current mode (translational movement mode or rotational movement mode) is indicated.

Further, the mode indicator 84a also serves as a pivot position indicator that indicates that the pivot position PP has been set.

Figure 10:
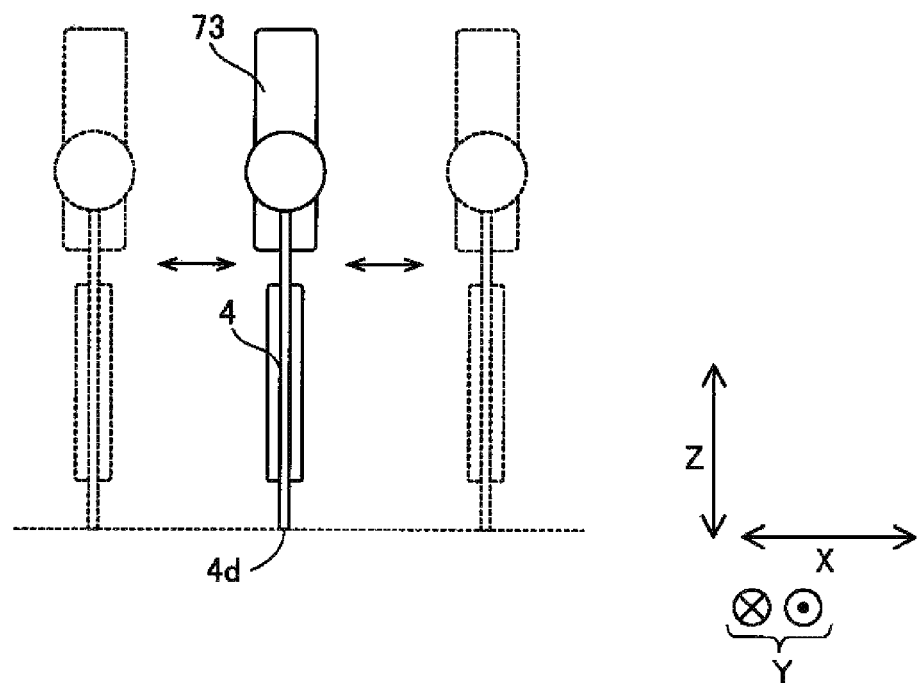
FIG. 10 is a diagram for explaining translational movements of the arm.
Figure 11:
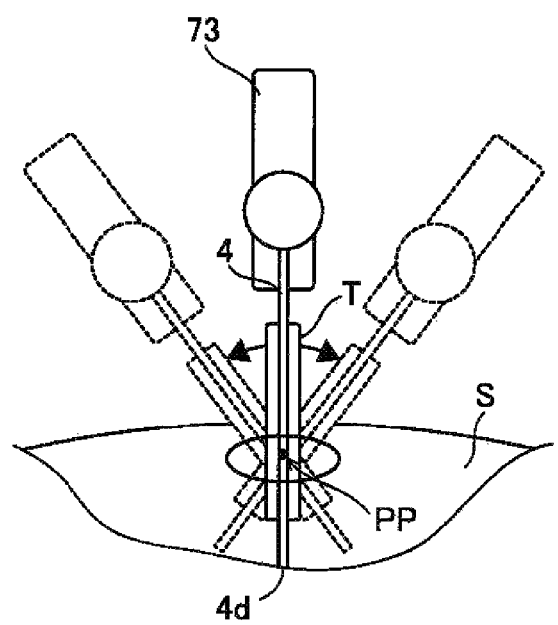
FIG. 11 is a diagram for explaining rotational movements of the arm.

As illustrated in FIG. 10, in the translational movement mode to translationally move the medical instrument 4, the arm 60 is moved in such a manner that the distal end 4d of the medical instrument 4 moves on the XY plane. Further, as illustrated in FIG. 11, in the rotational movement mode to rotationally move the medical instrument 4, when the pivot position PP is not set, the arm 60 is moved such that the medical instrument 4 is rotated around the forceps 4b, and when the pivot position PP is set, the arm 60 is moved such that the medical instrument 4 is rotated around the pivot position PP as a fulcrum. The medical instrument 4 is rotationally moved in the state where the shaft 4c of the medical instrument 4 is inserted through the trocar T.

As illustrated in FIG. 12, the arm 60 is provided with the plurality of servomotors M1, a plurality of encoders E1, and a plurality of speed reducers (not illustrated), so as to correspond to the plurality of joint portions 64 of the arm portion 61. The encoder E1 is configured to detect the rotation angle of the servomotor M1. The speed reducer is configured to reduce the rotation of the servomotor M1 to increase the torque.

As illustrated in FIG. 12, the translational movement mechanism 70 includes the servomotors M2 for rotating the rotors (rotation members) provided in the driven unit 4a of the medical instrument 4, a servomotor M3 for translationally moving the medical instrument 4, encoders E2, an encoder E3, and speed reducers (not illustrated). The encoders E2 and the encoder E3 are configured to detect the rotation angles of the servomotors M2 and the servomotor M3, respectively. The speed reducers are configured to reduce the rotations of the servomotors M2 and the servomotor M3 to increase the torque thereof.

The positioner 40 is provided with a plurality of servomotors M4, a plurality of encoders E4, and a plurality of speed reducers (not illustrated), so as to correspond to the plurality of joints 43 of the positioner 40. The encoders E4 detect the rotation angles of the servomotors M4. The speed reducers are configured to reduce the rotations of the servomotors M4 to increase the torque thereof.

The medical trolley 3 is provided with servomotors M5 that drive a plurality of front wheels (not illustrated) of the medical trolley 3 respectively, encoders E5, and speed reducers (not illustrated). The encoders E5 detect the rotation angles of the servomotors M5. The speed reducer is configured to reduce the rotation of the servomotor M5 to increase the torque.

The control unit 31 of the medical trolley 3 includes an arm control unit 31a that controls the movement of the plurality of arms 60 based on commands, and a positioner control unit 31b that controls the movement of the positioner 40 and driving of the front wheel (not illustrated) of the medical trolley 3 based on commands. A servo control unit C1 that controls the servomotors M1 for driving the arm 60 is electrically connected to the arm control unit 31a. Further, the encoder E1 that detects the rotation angle of the servomotor M1 is electrically connected to the servo control unit C1.

A servo control unit C2 that controls the servomotors M2 for driving the medical instrument 4 is electrically connected to the arm control unit 31a. The encoders E2 that detect the rotation angles of the servomotors M2 are electrically connected to the servo control unit C2. The servo control unit C3 that controls the servomotor M3 for translationally moving by the translational movement mechanism 70 is electrically connected to the arm control unit 31a. The encoder E3 for detecting the rotation angle of the servomotor M3 is electrically connected to the servo control unit C3.

The operation command inputted to the remote control apparatus 2 is inputted to the arm control unit 31a. The arm control unit 31a generates position commands based on the inputted operation command and the rotation angles detected by the encoders E1 (E2, E3), and outputs the position commands to the servo control units C1 (C2, C2). The servo control units C1 (C2, C3) generate torque commands based on the position commands inputted from the arm control unit 31a and the rotation angles detected by the encoders E1 (E2, E3), and output the torque commands to the servomotors M1 (M2, M3). As a result, the arm 60 is moved so as to comply with the operation command inputted to the remote control apparatus 2.

As illustrated in FIG. 12, the control unit 31 (arm control unit 31a) is configured to operate the arm 60 based on an input signal from the joystick 82 of the operation unit 80. Specifically, the arm control unit 31a generates position commands based on the input signal (operation command) inputted from the joystick 82 and the rotation angles detected by the encoders E1, and outputs the position commands to the servo control units C1. The servo control unit C1 generates torque commands based on the position command inputted from the arm control unit 31a and the rotation angles detected by the encoders E1, and outputs the torque commands to the servomotors M1. As a result, the arm 60 is moved so as to follow the operation command inputted to the joystick 82.

The control unit 31 (arm control unit 31a) is configured to operate the arm 60 based on an input signal from the switch section 83 of the operation unit 80. Specifically, the arm control unit 31a generates position commands based on the input signal (operation command) inputted from the switch section 83 and the rotation angles detected by the encoders E1 or E3, and outputs the position commands to the servo control units C1 or C3. The servo control units C1 or C3 generate torque commands based on the position command inputted from the arm control unit 31a and the rotation angles detected by the encoders E1 or E3, and outputs the generated torque commands to the servomotors M1 or M3. As a result, the arm 60 is moved so as to follow the operation command inputted to the switch section 83.

As illustrated in FIG. 12, the servo control units C4 that control the servomotors M4 for moving the positioner 40 are electrically connected to the positioner control unit 31b. The encoders E4 that detect the rotation angles of the servomotors M4 are electrically connected to the servo control units C4. The servo control units C5 that control the servomotors 5 for driving the front wheel (not illustrated) of the medical trolley 3 are electrically connected to the positioner control unit 31b. The encoders E5 that detect the rotation angles of the servomotors M5 are electrically connected to the servo control units C5.

An operation command regarding setting of the preparation position and the like is inputted from the input device 33 to the positioner control unit 31b. The positioner control unit 31b generates position commands based on the operation command inputted from the input device 33 and the rotation angle detected by the encoder E4, and outputs the position commands to the servo control units C4. The servo control unit C4 generates torque commands based on the position command inputted from the positioner control unit 31b and the rotation angles detected by the encoders E4, and outputs the torque commands to the servomotors M4. As a result, the positioner 40 is moved so as to follow the operation command inputted to the input device 33. Similarly, the positioner control unit 31b moves the medical trolley 3 based on the operation command from the input device 33.

Here, in a first embodiment, the surgical operation system 100 includes an image processing device 8. The image processing device 8 generates a graphical user interface G (see FIG. 14) and displays, on the monitor 24 of the remote control apparatus 2, the graphical user interface G superimposed on the image gr (see FIG. 13) captured by the endoscope 6. The image processing device 8 is configured to obtain from the endoscope 6 the image gr captured by the endoscope 6. The image processing device 8 obtains, from the arm control unit 31a, information on the movable range of the arm 60 and information on the current position of the arm 60. Further, the image processing device 8 obtains, from the remote control apparatus 2, information on the operable range of the operation handle 21 and information on the current position of the operation handle 21. Note that the image processing device 8 is an example of an "control device" or a "controller".

Figure 14:
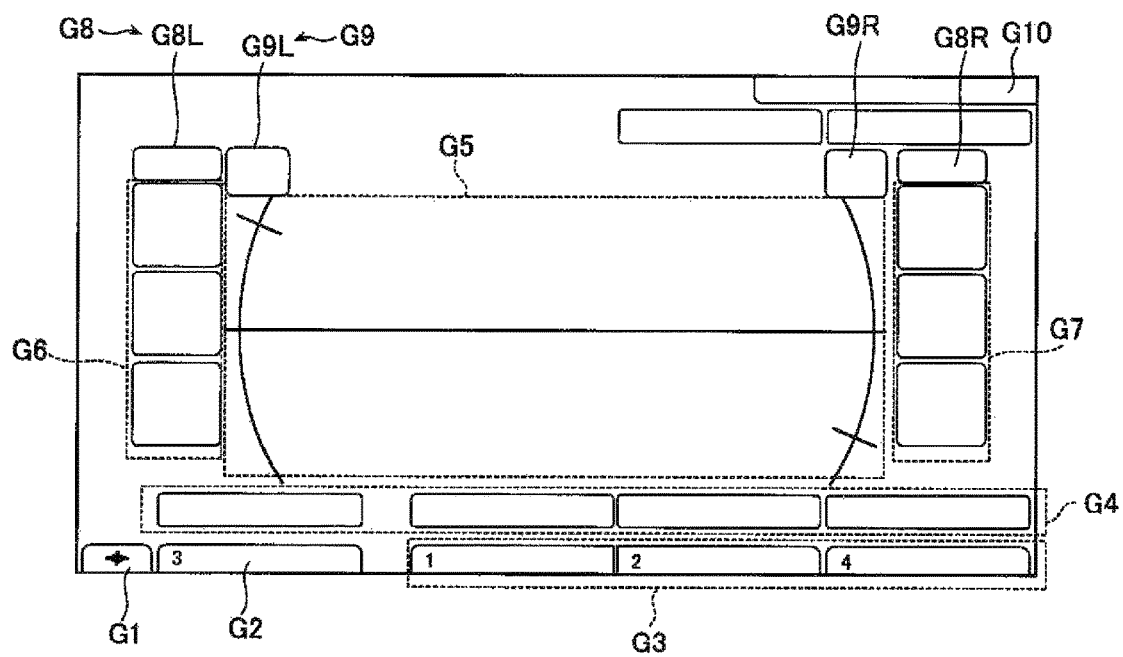
FIG. 14 is a diagram illustrating areas in the graphical user interface.
Figure 15A:
FIGS. 15A, 15B, and 15C are diagrams for explaining displays of a clutch area.
Figure 15B:
Figure 15C:
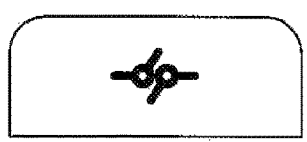
Figure 16:
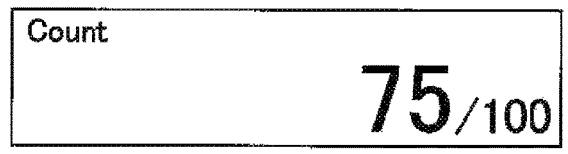
FIG. 16 is a diagram for explaining a display of a medical equipment area.

As illustrated in FIG. 14, the graphical user interface G includes a clutch area G1. A state of the clutch pedal 22b is displayed in the clutch area G1 as illustrated in FIGS. 15A, 15B, and 15C. FIG. 15A illustrates the clutch area in a state (OFF state) in which the clutch pedal 22b is not depressed. FIG. 15B illustrates the clutch area in a state (hover state) in which the operator puts his/her foot on the clutch pedal 22b. FIG. 15C illustrates the clutch area in a state (ON state) in which the clutch pedal 22b is depressed.

As illustrated in FIG. 14, the graphical user interface G includes a camera area G2. In the camera area G2, a state of the camera pedal 22c is displayed.

As illustrated in FIG. 14, the graphical user interface G includes a hand area G3. In the hand area G3, a state of each arm 60 and states of the coagulation pedal 22e and the cutting pedal 22d are displayed. The clutch area G1, the camera area G2, and the hand area G3 are displayed in a lower side portion on the monitor 24.

As illustrated in FIG. 14, the graphical user interface G includes a medical instrument area G4. In the medical instrument area G4, a ratio of the current number of times of use to the maximum number of times of use (see FIG. 16) of the medical instrument 4 attached to the arm 60 is displayed. When the current number of uses of the medical instrument becomes equal to the maximum number of uses of the medical instrument, the current number of uses is displayed in red. Further, when the medical instrument 4 is not attached to the arm 60, nothing is displayed in the medical instrument area G4. The medical instrument area G4 is displayed above the clutch area G1, the camera area G2, and the hand area G3 on the monitor 24.

As illustrated in FIG. 14, the graphical user interface G includes a level device area G5. In the level device area G5, information on the angle of the endoscope 6 is displayed. The level device area G5 is displayed only while the camera pedal 22c is depressed.

Figure 17A:
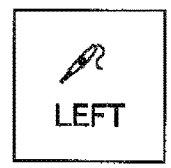
FIGS. 17A, 17B, and 17C are diagrams for explaining displays of a left pop-up area.
Figure 17B:
Figure 17C:
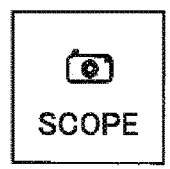
Figure 18:
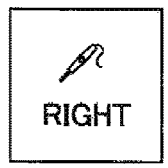
FIG. 18 is a diagram for explaining a display of a right pop-up area.

As illustrated in FIG. 14, the graphical user interface G includes a left pop-up area G6. In the left pop-up area G6, the icons illustrated in FIGS. 17A to 17C are displayed in the hover state, which is a state where the foot is placed on the foot pedal 22. FIG. 17A illustrates an icon displayed when the foot is placed on the coagulation pedal 22eL and/or the cutting pedal 22dL. FIG. 17B illustrates an icon displayed when the foot is placed on the clutch pedal 22b. FIG. 17C illustrates an icon displayed when the foot is placed on the camera pedal 22c. The left pop-up area G6 is displayed in a left side portion on the monitor 24.

As illustrated in FIG. 14, the graphical user interface G includes a right pop-up area G7. In the right pop-up area G7, an icon (FIG. 18) is displayed when the foot is placed on the coagulation pedal 22eR and/or the cutting pedal 22dR. The right pop-up area G7 is displayed in a right side portion on the monitor 24.

In a first embodiment, as illustrated in FIG. 14, the graphical user interface G includes a first area G8 that displays a first graphical display GR1 (see FIG. 19) indicating a movable range of the arm 60 and an operable range of the operation handle 21, which is a range where the operation handle 21 can be operated in the movable range of the arm 60. The graphical user interface G also includes a second area G9 that is different from the first area G8. The second area G9 displays a second graphical display GR2 (see FIG. 20) indicating a required operation of the operation handle 21 to return (reposition, reset) the operation handle 21 to the inside of the operable range and/or to return (reposition, reset) the arm 60 to the inside of the movable range. Note that in a first embodiment, the second graphical display GR2 indicates the required operation to return the operation handle 21 to the inside of the operable range and to return the arm 60 to the inside of the movable range.

In a first embodiment, the movable range of the arm 60 is a movable range of joints among joints JT9 to JT12 about which the shaft 4c is rotated. The movable range of the arm 60 is set to a rotational angle of 540 degrees having 270 degrees in the positive rotational direction and 270 degrees in the negative rotational direction. In a first embodiment, the operable range of the operation handle 21 is a movable range of the joint A7 (the joint JT7), and is a rotational angle of 540 degrees having 270 degrees in the positive rotational direction and 270 degrees the negative rotational direction.

Further, the second graphical display GR2 is appeared (displayed) when the angle to the end (the boundary) of the operable range of the operation handle 21 becomes equal to or less than a first threshold value and/or when the angle to the end (the boundary) of the movable range of the arm 60 becomes equal to or less than a second threshold value. Note that, in a first embodiment, the second graphical display GR2 is appeared (displayed) when the angle to the end (the boundary) of the operable range of the operation handle 21 becomes equal to or less than a first threshold value "and" when the angle to the end (the boundary) of the movable range of the arm 60 becomes equal to or less than a second threshold value. Each of the first threshold value and the second threshold value is set to, for example, 10°.

Further, in a first embodiment, the number of arms 60 that can be operated by the operation handle 21 is two. For example, the operation handle 21L operates the left arm 60L (for example, the arm 60a, see FIG. 1) that supports the medical instrument 4. Further, the operation handle 21R operates the right arm 60R (for example, the arm 60d, see FIG. 1) that supports the medical instrument 4. Then, the first area G8 that displays the first graphical display GR1 is divided to a first area G8L for the left arm 60L and a first area G8R for the right arm 60R, and the second area G9 that displays the second graphical display GR2 is divided to a second area G9L for the left arm 60L and a second area G9R for the right arm 60R. Note that the left arm 60L and the right arm 60R are examples of a "first manipulator" and a "second manipulator".

Specifically, in a first embodiment, the first area G8L and the second area G9L for the left arm 60L are displayed on one side (the left side) in the left-right direction in the monitor 24. The first area G8R and the second area G9R for the right arm 60R are displayed on the other side (the right side) in the left-right direction in the monitor 24. The first area G8L and the second area G9L are displayed in the upper left side (above the left pop-up area G6) in the monitor 24. The first area G8R and the second area G9R are displayed in the upper right side (above the right pop-up area G7) in the monitor 24. Further, in the monitor 24, height positions of the first area G8L, the second area G9L, the first area G8R, and the second area G9R are substantially the same as each other.

Figure 19:
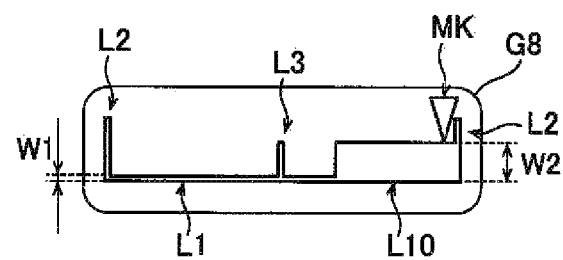
FIG. 19 is a diagram for explaining a first graphical display.

Further, in a first embodiment, as illustrated in FIG. 19, each of the movable range of the arm 60 and the operable range of the operation handle 21 is represented by a length of a line on the image gr. The movable range of the arm 60 is represented by the length of a line L1 extending in the horizontal direction on the monitor 24. At both ends of the line L1 extending in the horizontal direction, boundary lines L2 (which indicate mechanical limit points of the arm 60) extending in the vertical direction are provided.

Further, in a first embodiment, the display of the movable range of the arm 60 represented by the length of the line L1 further includes a line L3 that extends in the vertical direction and indicates the center of the movable range. Note that the line L3 is an example of a "mark". The length of the line L3 is smaller than the length of each of the boundary lines L2.

The operable range of the operation handle 21 is represented by a line L10 extending in the horizontal direction. The width W2, in the vertical direction, of the line L10 is larger than the width W1, in the vertical direction, of the line L1.

Further, in a first embodiment, the length of the line L1 representing the movable range of the arm 60 is maintained (fixed), and the length of the line L10 representing the operable range of the operation handle 21 is changeable to expand and contract along with the movement of the operation handle 21. When the operation handle 21 is operated (rotated) and thus the operable range of the operation handle 21 becomes smaller, the length of the line L10 displayed becomes smaller. When the operation handle 21 is operated (rotated) and thus the operable range of the operation handle 21 becomes larger, the length of the line L10 displayed becomes larger.

Here, the movement amount of the medical instrument 4 is scaled with respect to the operation amount received by the operation handle 21. That is, the ratio of the operation amount of the operation handle 21 to the movement amount of the medical instrument 4 is not a one-to-one correspondence. Therefore, the amount of movement of the medical instrument 4 is smaller than the operation amount received by the operation handle 21. As a result, even when the operation handle 21 is operated to the end (the boundary) of the operable range, the medical instrument 4 does not necessarily reach the end (the boundary) of the operable range. At the time when operation handle 21 reaches the end of the operable range of the operation handle 21, the operator performs a clutch operation to temporarily disconnect the operational connection between the medical instrument 4 (the arm 60) and the operation handle 21, and returns the operation handle 21 to the original position or the like, so as to expand the operable range of the operation handle 21. That is, the operable range (the line L1) of the arm 60 (the medical instrument 4) and the operable range (the line L10) of the operation handle 21 have the lengths different from each other and are deviated (biased) from each other.

Therefore, in a first embodiment, the line L10 representing the operable range of the operation handle 21 and the line L1 representing the movable range of the arm 60 are displayed in an overlapped manner in such that the deviated amount (the biased amount) between the operable range of the operation handle 21 and the movable range of the arm 60 can be identified. Specifically, the lines L1 and L10 are displayed in a manner that the lower end of the line L10 representing the operable range of the operation handle 21 touches (overlaps) the line L1 representing the movable range of the arm 60.

Further, in a first embodiment, in order to identify a direction in which the operable range of the operation handle 21 is deviated from (biased with respect to) the movable range of the arm 60, the line L10 representing the operable range of the operation handle 21 and the line L1 representing the movable range of the arm 60 are displayed in such a manner that the line L10 is deviated (biased) in the deviation direction (the biased direction) with respect to the line L1 representing the movable range of the arm 60. For example, in an example illustrated in FIG. 19, the line L10 representing the operable range of the operation handle 21 is shifted to the right side within the line L1 representing the movable range of the arm 60. In this case, the operation handle 21 can be operated only in the operable range of the operation handle 21 (the line L10) that is shifted to the right side in the movable range of the arm 60 (the line L1).

Further, in a first embodiment, the first graphical display GR1 further indicates the current position of the arm 60. As the current position of the arm 60, the current position of the arm 60 within the operable range of the operation handle 21 is displayed. Specifically, a mark MK having a downward triangular shape representing the current position of the arm 60 is displayed above the line L10 (the operable range of the operation handle 21), for example.

Figure 20:
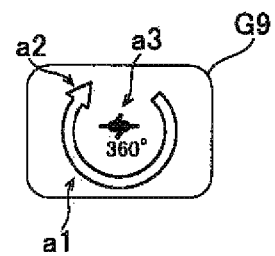
FIG. 20 is a diagram for explaining a second graphical display.

Further, as illustrated in FIG. 20, the second graphical display GR2 is displayed which indicates a required operation of the operation handle 21 to return the operation handle 21 to the inside of the operable range of the operation handle 21 and/or (in a first embodiment, "and") return the arm 60 to the inside of the operable range of the arm 60. The second graphical display GR2 indicates the direction in which the operation handle 21 is to be rotated. The direction in which the operation handle 21 is to be rotated is represented by an arc a1 with an arrow a2 provided at a leading end of the arc a1 corresponding to the direction in which the operation handle 21 is to be rotated. In an example illustrated in FIG. 20, the arc a1 with the clockwise arrow a2 is displayed to indicate that the operation handle 21 is required to be rotated in the clockwise direction by the rotation angle of 360 degrees.

Further, in a first embodiment, the length of the arc a1 is changeable corresponding to the rotation angle of the operation handle 21. The rotation angle of the operation handle 21 indicated by the second graphical display GR2 includes two types of 360 degrees and 180 degrees. Thus, the arc a1 has two types in which one is a relatively long arc a1 corresponding to and indicating the rotational angle of 360 degrees and the other is a relatively short arc a1 corresponding to and indicating the rotational angle of 180 degrees.

Further, in a first embodiment, the angle by which the operation handle 21 is required to be rotated is further displayed in the second area G9. Specifically, in the second area G9, a value "360°" or "180°" is displayed indicating the rotation angle of the operation handle 21 by which the operation handle 21 is required to be rotated. The value "360°" or "180°" is displayed inside the arc a1 having the arrow a2 that indicates the direction in which the operation handle 21 is to be rotated.

Further, in a first embodiment, in the second area G9, a graphical display a3 for a clutch operation is also displayed to indicate that the clutch operation is required for temporarily disconnecting the operational connection between the arm 60 and the operation handle 21. The clutch operation graphical display a3 is displayed inside the arc a1 having the arrow a2 that indicates the direction in which the operation handle 21 is to be rotated. Further, the clutch operation graphical display a3 is displayed above the value "360°" or "180°".

Further, in a first embodiment, as illustrated in FIG. 14, the first area G8 and the second area G9 are provided adjacent to each other. Specifically, in the monitor 24, the first area G8 and the second area G9 are provided adjacent to each other in the horizontal direction (side by side).

Figure 21:
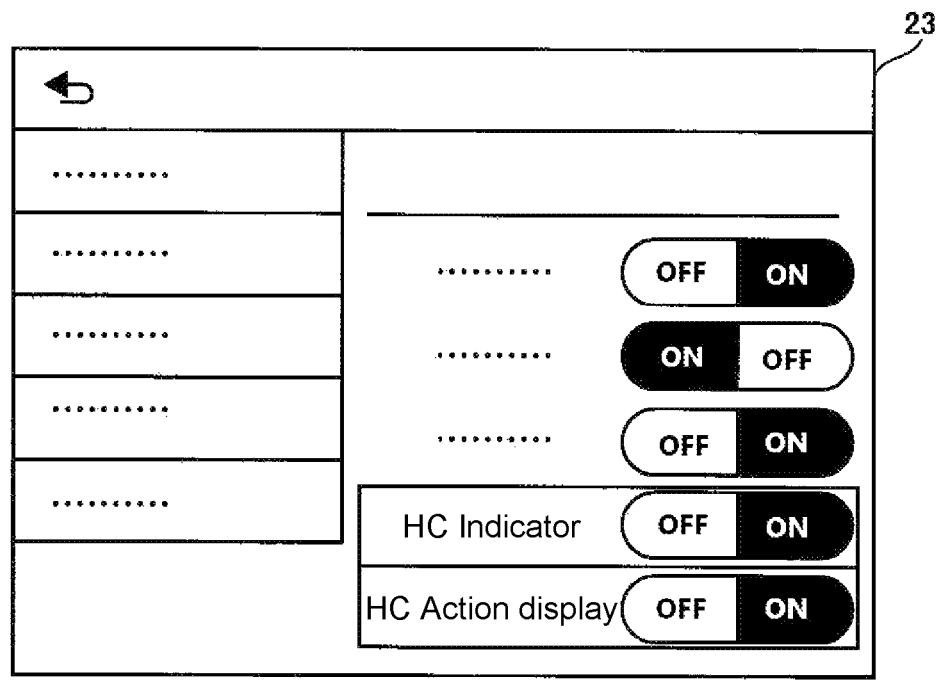
FIG. 21 is a diagram for explaining a display of a touch panel of a remote control apparatus.

Further, in a first embodiment, the first graphical display GR1 and the second graphical display GR2 are configured to transition between a displayed state and a non-displayed state. Specifically, as illustrated in FIG. 21, on the touch panel 23 of the remote control apparatus 2, "ON" and "OFF" buttons for turning on and off an "HC indicator" and "ON" and "OFF" buttons for turning on and off an "HC action display" are displayed. Note that the "HC" means the hand controller (the operation handle 21). When the "ON" button for turning on the "HC indicator" is selected on the touch panel 23 of the remote control apparatus 2, the first graphical display GR1 is always displayed. When the "OFF" button for turning off the "HC indicator" is selected on the touch panel 23 of the remote control apparatus 2, the first graphical display GR1 is not displayed. With this configuration, it is possible to set not to display the "HC indicator" (the first graphical display GR1), which may be less necessary for an operator who is skilled in operation with the operation handle 21 to operate the arm 60.

Further, in a first embodiment, the second graphical display GR2 is displayed when the clutch pedal 22b is operated. Further, the second graphical display GR2 is displayed when executing the connecting operation between the arm 60 and the operation handle 21. Specifically, in the state where the "ON" button for the "HC action display" is selected, the second graphical display GR2 is displayed in one of the following conditions: (i) when the connecting operation (matching grip: synchronization of the grip of the operation handle 21 with the distal end of the medical instrument 4) is being performed; (ii) when the clutch pedal 22b is being depressed; (iii) when the angle to the end of the operable range of the operation handle 21 is equal to or less than the first threshold value (for example, 10°); and (iv) when the angle to the end of the movable range of the arm 60 is equal to or less than the second threshold value (for example, 10°). Further, when the "OFF" button for turning off the "HC action display" is selected, the second graphical display GR2 is not displayed.

As illustrated in FIG. 14, the graphical user interface G includes a status area G10. In the status area G10, information such as the remaining amount of the built-in battery of the medical manipulator 1, the brightness/contrast of the monitor 24, the lap time, the elapsed time of the surgery, and the like are displayed.

Next, an operation to correct the deviation between the movable range of the arm 60 and the operable range of the operation handle 21 is described.

(Case A)

As illustrated in FIG. 22, in Case A, the first graphical display GR1 is displayed in the first area G8, in which the line L10 which indicates the operable range of the operation handle 21 is displayed with a relatively short length and is shifted to the left side on the line L1 which indicates the movable range of the arm 60, and the triangular mark MK which indicates the current position of the arm 60 is located at the right end of the line L10. That is, the operation handle 21 has a margin to the left end of the operable range of the operation handle 21 and thus can be rotated in the left direction, but the operation handle 21 has no margin to the right end of the operable range and thus cannot be rotated in the right direction. Further, the arm 60 has margins to the left end and the right end of the movable range of the arm 60 and thus can be rotated in the left and right directions. Accordingly, in Case A, it may be necessary to widen the operable range of the operation handle 21 to the right.

Therefore, in order to notify the operator that an operation is required to expand the operable range of the operation handle 21 to the right, the second graphical display GR2 is displayed in the second area G9 including the clutch operation graphical display a3, the arc a1 with the arrow a2 indicating that the operation handle 21 is required to be rotated in the counterclockwise direction by 360 degrees, and the value "360°." Then, the operator, who recognizes the second graphical display GR2 in the second area G9, rotates (moves) the operation handle 21 in the counterclockwise direction by 360 degrees while depressing the clutch pedal 22b by the foot, so as to expand the operable range of the operation handle 21 to the right. With this operation, the operable range of the operation handle 21 is expanded (moved) to the right and thus the display of the second area G9 (the second graphical display GR2) disappears (is ended).

(Case B)

As illustrated in FIG. 23, in Case B, the first graphical display GR1 is displayed in the first area G8, in which the line L10 (the operable range of the operation handle 21) has a relatively short length and is shifted to the right side on the line L1 (the movable range of the arm 60), and the triangular mark MK (the current position of the arm 60) is located at the left end of the line L 10. That is, the operation handle 21 has no margin to the left end of the operable range of the operation handle 21 but has a margin to the right end of the operable range of the operation handle 21. Further, the arm 60 has margins to the left end and the right end of the movable range of the arm 60. In Case B, it may be necessary to widen the operable range of the operation handle 21 to the left.

Accordingly, in order to notify the operator that an operation is required to expand the operable range of the operation handle 21 to the left, the second graphical display GR2 is displayed in the second area G9, including the clutch operation graphical display a3, the arc a1 with the arrow a2 indicating that the operation handle 21 is required to be rotated in the clockwise direction by 360 degrees, and the value "360°." Then, the operator, who recognizes the second graphical display GR2 in the second area G9, rotates (moves) the operation handle 21 in the clockwise direction by 360 degrees while depressing the clutch pedal 22b, so as to expand the operable range of the operation handle 21 to the left. With this operation, the operable range of the operation handle 21 is expanded (moved) to the left, and thus the display of the second area G9 (the second graphical display GR2) disappears.

(Case C)

As illustrated in FIG. 24, in Case C, the first graphical display GR1 is displayed in the first area G8, in which the triangular mark MK (the current position of the arm 60) is displayed at the left end of the line L10 (the operable range of the operation handle 21) and at the left end of the line L1 (the movable range of the arm 60). That is, the operation handle 21 has no margin to the left end of the operable range of the operation handle 21 but has a margin to the right end of the operable range of the operation handle 21. Further, the arm 60 has no margin to the left end of the movable range of the arm 60 but has a margin to the right end of the movable range of the arm 60. In Case C, it may be necessary to move the arm 60 to a position where the arm 60 is movable in both the left direction and the right direction.

Accordingly, in order to notify the operator that the arm 60 is required to be moved to the right, the second graphical display GR2 is displayed in the second area G9, including the arc a1 with the arrow a2 indicating to rotate the operation handle 21 by 360 degrees in the clockwise direction, and the value "360°". Then, the operator, who recognizes the second graphical display GR2 in the second area G9, rotates the operation handle 21 in the clockwise direction by 360 degrees without depressing the clutch pedal 22b, so as to move the arm 60 to the right. With this operation, the arm 60 is moved to a position where the arm 60 is movable in both the right and left directions and thus the display of the second area G9 (the second graphical display GR2) disappears.

(Case D)

As illustrated in FIG. 25, in Case D, the first graphical display GR1 is displayed in the first area G8, in which the triangular mark MK (the current position of the arm 60) is located at the right end of the line L10 (the operable range of the operation handle 21) and at the right end of the line L1 (the movable range of the arm 60). That is, the operation handle 21 has a margin to the left end of the operable range of the operation handle 21 but has no margin to the right end of the operable range of the operation handle 21. Further, the arm 60 has a margin to the left end of the movable range of the arm 60 but has no margin to the right end of the movable range of the arm 60. Accordingly, in Case D, it may be necessary to move the arm 60 to a position where the arm 60 is operable in both the left direction and the right direction.

Accordingly, in order to notify the operator that the arm 60 is required to be moved to the left, the second graphical display GR2 is displayed in the second area G9, including the arc a1 with the arrow a2 indicating to rotate the operation handle 21 in the counterclockwise direction by 360 degrees, and the value "360°". Then, the operator, who recognizes the second graphical display GR2 in the second area G9, rotates (operates) the operation handle 21 in the counterclockwise direction by 360 degrees without depressing the clutch pedal 22b, so as to move the arm 60 to the left. With this operation, the arm 60 is moved to a position where the arm 60 is movable in both the right and left directions and thus the display of the second area G9 (the second graphical display GR2) disappears.

(Display Method)

Figure 26:
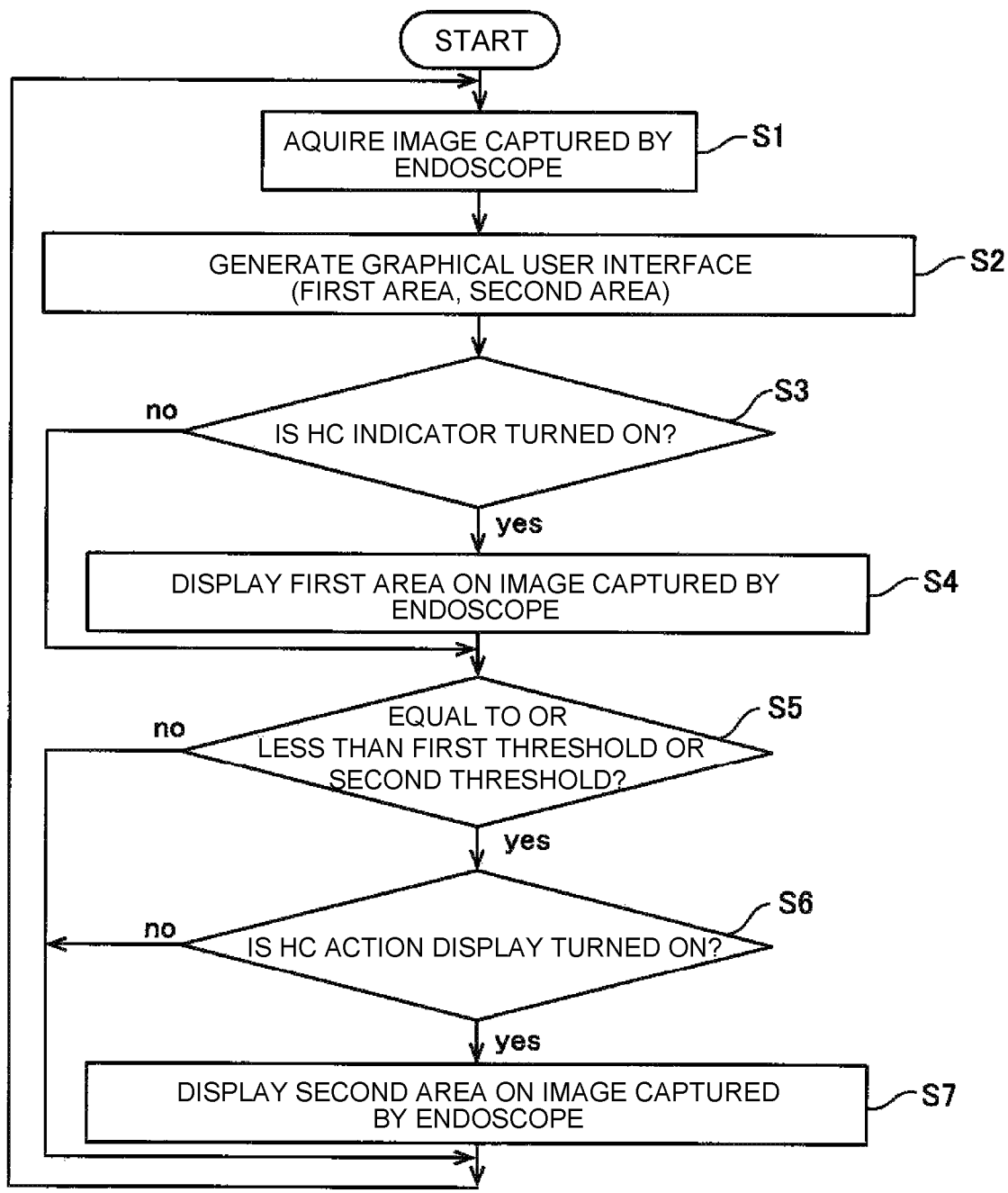
FIG. 26 is a diagram illustrating a flowchart for explaining a display method of the surgical operation system according to a first embodiment.

Next, with reference to FIG. 26, a method of displaying the graphical user interface G on the monitor 24 in the surgical operation system 100 is described. The graphic user interface G is generated by the image processing device 8. In the following description, an operation of displaying the second graphical display GR2 during the processing of the matching grip and an operation of displaying the second graphical display GR2 when the clutch pedal 22b is depressed are omitted.

First, in step S1, the image processing device 8 acquires the image gr of the surgical site captured by the endoscope 6.

Next, in step S2, in a first embodiment, the image processing device 8 generates the graphical user interface G including the first area G8 that displays the first graphical display GR1 indicating the movable range of the arm 60 and the operable range of the operation handle 21 where the operation handle 21 is movable in the movable range of the arm 60. Further, the image processing device 8 generates the second area G9 that is different from the first area G8 and that displays the second graphical display GR2 indicating the required operation of the operation handle 21 to return the arm 60 to the inside of the movable range of the arm 60 (to return the arm 60 toward the center of the movable range of the arm 60) and to return the operation handle 21 to the inside of the operable range of the operation handle 21 (to return the operation handle 21 toward the center of the operable range of the operation handle 21).

Next, in step S3, the image processing device 8 determines whether or not the "ON" button is selected in the "HC indicator" setting on the touch panel 23 of the remote control apparatus 2.

Next, in the case of "Yes" in step S3, the process proceeds to step S4, and in step 4, the image processing device 8 displays, on the monitor 24, the first area G8 displaying the first graphical display GR1 on the image gr captured by the endoscope 6 in the overlapped manner and the process proceeds to step S5. In the case of "No" in step S3, the process proceeds to step S5.

Next, in step S5, the image processing device 8 determines if the angle to the end of the movable range of the arm 60 is equal to or less than the first threshold value, or the angle to the end of the operable range of the operation handle 21 is equal or less than the second threshold value.

Next, in the case of "Yes" in step S5, the process proceeds to step S6, and, in step S6, the image processing device 8 determines whether or not the "ON" button is selected in the "HC action display" setting on the touch panel 23 of the remote control apparatus 2.

In the case of "Yes" in step S6, the process proceeds to step S7, and the image processing device 8 displays, in the monitor 24, the second area G9 displaying the second graphical display GR2 on the image gr captured by the endoscope 6. In the case of "No" in step S5 or step S6, the process returns to step S1.

The operation of steps S1 to S7 are always performed during the operation of each of the two arms 60 being operated by the operation handles 21.

Effects of First Embodiment

In a first embodiment, the following effects can be obtained.

As described above, in the surgical operation system 100 and the display method according to a first embodiment, the graphical user interface G includes the second area G9 that is different from the first area G8 and that displays the second graphical display GR2 indicating the required operation of the operation handle 21 to return the arm 60 to the inside of the movable range of the arm 60 (to return the arm 60 toward the center of the movable range of the arm 60) and/or to return the operation handle 21 to the inside of the operable range of the operation handle 21 (to return the operation handle 21 toward the center of the operable range of the operation handle 21). Here, in the surgical operation system 100, the movement amount of the arm 60 may be scaled so as to be smaller than the operation amount received by the operation handle 21. In this case, even if the arm 60 is within the operable range, it is possible that the operation handle 21 is out of (at the end of) the operable range of the operation handle 21. Therefore, the operator may need to disconnect the operational connection between the operation handle 21 and the arm 60 and then return the operation handle 21 to the inside of the operable range of the operation handle 21. Further, while repeating such an operation, the arm 60 may reach the end of the movable range of the arm 60, and thus the operator may need to return the arm 60 to the inside of the operable range of the arm 60. In light of this, a first embodiment is configured as described above. Therefore, the operator can recognize a required operation of the operation handle 21 to return the operation handle 21 to the inside of the operable range and/or to return the arm 60 to the inside of the movable range of the arm 60, by visually recognizing the second area G9 of the graphical user interface G. As a result, the operator can easily recognize a required operation of the operation handle 21 to return the operation handle 21 to the inside of the operable range of the operation handle 21 and/or to return the arm 60 to the inside of the movable range of the arm 60.

Further, the graphical user interface G includes the first area G8 that displays the first graphical display GR1 indicating the movable range of the arm 60 and the operable range of the operation handle 21 where the operation handle 21 can be operated in the movable range of the arm 60. With this configuration, by visually checking the first area G8 of the graphical user interface G, the operator can easily recognize whether or not the operation handle 21 is approaching the end of the operable range of the operation handle 21, and whether or not the arm 60 is approaching the end of the movable range of the arm 60.

Further, in a first embodiment, as described above, the second graphical display GR2 is displayed, when the angle to the end of the operable range of the operation handle 21 becomes equal to or less than the first threshold value or the angle to the end of the movable range of the arm 60 becomes equal to or less than the second threshold value. With this configuration, when the angle to the end of the operable range of the operation handle 21 is larger than the first threshold value and/or when the angle to the end of the movable range of the arm 60 is larger than the second threshold value, the second graphical is not displayed. Therefore, it is possible to suppress the second graphical display GR2 from interfering with the operator's visual recognition of the monitor 24. Further, since the second graphical display GR2 is displayed when the angle to the end of the operable range of the operation handle 21 is equal to or less than the first threshold value and/or when the angle to the end of the movable range of the arm 60 is equal to or less than the second threshold value, the operator can easily recognize that the operation handle 21 has approached the end of the operable range of the operation handle 21 and/or the arm 60 has approached the end of the movable range of the arm 60.

Further, in a first embodiment, as described above, the arms 60 include the left arm 60L and the right arm 60R, and the operation handles 21 include the operation handle 21L for the left arm 60L and the operation handle 21R for the right arm 60R. The first area G8 for displaying the first graphical display GR1 is provided for each of the left arm 60L and the right arm 60R, and the second area G9 for displaying the second graphical display GR2 is provided for each of the left arm 60L and the right arm 60R. That is, the first areas G8 that display the first graphical displays GR1 for the left arm 60L and the right arm 60R are separately provided and the second areas G9 that display the second graphical displays GR2 for the left arm 60L and the right arm 60R are separately provided. As a result, the operator can easily distinguish between the operation of the operation handle 21L of the left arm 60L and the operation of the operation handle 21R for the right arm 60R.

Further, in a first embodiment, as described above, the operation handle 21L is arranged on one side (the left side) in the left-right direction and the operation handle 21R is on the other side (the right side) in the left-right direction in the remote control apparatus 2, as viewed from the operator or with respect to the monitor 24. The first area G8L and the second area G9L for the left arm 60L are displayed on the one side (the left side) in the left-right direction on the monitor 24, and the first area G8R and the second area G9R for the right arm 60R are displayed on the other side (the right side) in the left-right direction on the monitor 24. That is, the position of the first and second areas G8L and G9L for the left arm 60L and the position of the first and second areas G8R and G9R for the right arm 60R in the monitor 24 correspond to the position of the left operation handle 21L and the position of the right operation handle 21R in the left-right direction. Accordingly, the operator can more easily and intuitively distinguish between the required operation of the left operation handle 21L for the left arm 60L and the required operation of the right operation handle 21R for the right arm 60R.

Further, in a first embodiment, as described above, the first graphical display GR1 further indicates the current position of the arm 60. As a result, the operator can easily recognize the current position of the arm 60 by visually checking the first graphical display GR1.

Further, in a first embodiment, as described above, as the current position of the arm 60, the mark MK (indicating the current position of the arm 60) is displayed within the range of the line L10 (indicating the operable range of the operation handle 21). Thereby, the operator can easily recognize whether or not the arm 60 being operated by the operation handle 21 is approaching the end of the operable range of the handle 21 by visually checking the first graphical display GR1.

Further, in a first embodiment, as described above, the movable range of the arm 60 and the operable range of the operation handle 21 are represented by the lengths of the lines on the image gr. Thereby, the operator can intuitively recognize the movable range of the arm 60 and the operable range of the operation handle 21 according to the lengths of the lines.

Further, in a first embodiment, as described above, the length of the line L1 representing the movable range of the arm 60 is fixed, and the length of the line L10 representing the operable range of the operation handle 21 is changed to expand and contract as the operation handle 21 is moved. As a result, the operator can easily recognize the current state of the operable range of the operation handle 21 with respect to the fixed movable range of the arm 60 in real time.

Further, in a first embodiment, as described above, the line L10 representing the operable range of the operation handle 21 and the line L1 representing the movable range of the arm 60 are displayed in an overlapped manner such that the amount of deviation between the operable range of the operation handle 21 and the movable range of the arm 60 can be identified. Further, the line L10 representing the operable range of the operation handle 21 is biased (shifted) in the deviation direction with respect to the line L1 representing the movable range of the arm 60, such that the deviation direction of the operable range of the operation handle 21 with respect to the movable range of the arm 60 can be identified. Note that, the movement amount of the arm 60 may be scaled with respect to the operation amount received by the operation handle 21. In this case, deviation occurs between the length of the operable range of the operation handle 21 and the length of the movable range of the arm 60. In light of this, a first embodiment is configured as described above. Accordingly, the operator can intuitively recognize the amount of deviation between the operable range of the operation handle 21 and the movable range of the arm 60, and the deviation direction of the operable range of the operation handle 21 with respect to the movable range of the arm 60.

Further, in a first embodiment, as described above, the display of the movable range of the arm 60, indicated by the length of the line L1, further includes the line L3 indicating the center of the movable range. With this, the operator can intuitively recognize the center of the movable range of the arm 60.

Further, in a first embodiment, as described above, the second graphical display GR2 indicates the direction to rotate the operation handle 21. With this configuration, the operator can easily recognize the direction to rotate the operation handle 21, so that it is possible to suppress an erroneous operation of the operation handle 21 by the operator.

Further, in a first embodiment, as described above, the direction to rotate the operation handle 21 is represented by the arc a1 with the arrow a2 provided at the leading end of the arc a1 indicating the direction to rotate the operation handle 21. With this configuration, since the display of the arc a1 with the arrow a2 in the second graphical display GR2 corresponds to the required operation for the operator to rotate the operation handle 21, an erroneous operation of the operation handle 21 by the operator can be more easily suppressed.

Further, in a first embodiment, as described above, the arc a1 has the length corresponding to the rotation angle of the operation handle 21. With this configuration, the operator can intuitively recognize the amount of rotation of the operation handle 21, so that an erroneous operation of the operation handle 21 by the operator can be more effectively suppressed.

Further, in a first embodiment, as described above, the angle by which the operation handle 21 is required to be rotated is further displayed in the second area G9. With this configuration, the operator can easily recognize the rotation amount of the operation handle 21 by recognizing the angle (numerical value). Thus, the operator can rotate the operation handle 21 by an appropriate amount.

Further, in a first embodiment, as described above, the remote control apparatus 2 further includes the clutch pedal 22b for executing a clutch operation to temporarily disconnect the operational connection between the arm 60 and the operation handle 21. With this configuration, the operator can easily perform the clutch operation using the clutch pedal 22b.

Further, in a first embodiment, as described above, when the clutch operation is required, the second area G9 displays the clutch operation graphical display a3 indicating that the clutch operation is required. With this configuration, the operator O can easily recognize that the clutch operation is required. As a result, it is possible to prevent the operator from operating the operation handle 21 without performing the clutch operation (without disconnecting the operational connection between the arm 60 and the operation handle 21).

Further, in a first embodiment, as described above, the second graphical display GR2 is displayed when the clutch pedal 22b is operated. As a result, the operator can easily confirm the deviation between the arm 60 and the operation handle 21 when the clutch pedal 22b is operated.

Further, in a first embodiment, as described above, the second graphical display GR2 is displayed when the connecting operation between the arm 60 and the operation handle 21 is performed. With this configuration, the operator can easily recognize the deviation between the arm 60 and the operation handle 21 immediately after the connecting operation between the arm 60 and the operation handle 21.

Further, in a first embodiment, as described above, the first area G8 and the second area G9 are arranged adjacent to each other. Thereby, unlike the case where a relatively large distance is provided between the first area G8 and the second area G9, the operator can easily visually recognize both of the first area G8 and the second area G9.

Further, in a first embodiment, as described above, the first graphical display GR1 and the second graphical display GR2 are configured to be able to switch between the displayed state and the non-displayed state. Thereby, the display state and the non-display state of the first graphical display GR1 and the second graphical display GR2 can be selected according to the preference of the operator.

Second Embodiment

With reference to FIGS. 27 and 28, an operation to correct the deviation between the movable range of the arm 60 and the operable range of the operation handle 21 according to a second embodiment is described below. In a second embodiment, the deviation between the movable range of the arm 60 and the operable range of the operation handle 21 is corrected by performing two operations (Operation 1 and Operation 2).

(Case E)

As illustrated in FIG. 27, in Case E, the first graphical display GR1 is displayed in the first area G8, in which the line L10 indicating the operable range of the operation handle 21 is displayed with a relatively short length and is shifted to the left side on the line L1 indicating the movable range of the arm 60), and the triangular mark MK indicating the current position of the arm 60 is located at the right end of the line L10 (the operable range of the operation handle 21). That is, the operation handle 21 has a margin to the left end of the operable range of the operation handle 21 but has no margin to the right end of the operable range of the operation handle 21. Further, the arm 60 has margins to the left end and the right end of the movable range of the arm 60. Accordingly, in Case E, it may be necessary to widen the operable range of the operation handle 21 to the right.

Therefore, the second graphical display GR2 is displayed in the second area G9, including the clutch operation graphical display a3, the arc a1 with the arrow a2 indicating the operation handle 21 is required to be rotated in the counterclockwise direction by 360 degrees, and the value "360°." Then, the operator, who recognizes the second graphical display GR2 in the second area G2, rotates the operation handle 21 in the counterclockwise direction by 360 degrees while depressing the clutch pedal 22b (Operation 1), so that the operable range of the operation handle 21 is expanded to the right. With this operation (Operation 1), the second graphical display GR2 is further displayed in the second area G9, including the clutch operation graphical display a3, the arc a1 with the arrow a2 indicating to rotate the operation handle 21 in the counterclockwise direction by 180 degrees, and the value "180°". Then, the operator, who recognizes the display in the second area G9, rotates the operation handle 21 in the counterclockwise direction by 180 degrees while depressing the clutch pedal 22b (operation 2), so that the operable range of the operation handle 21 is expanded to the right. With this operation (Operation 2), the display of the second area G9 (the second graphical display GR2) disappears.

(Case F)

As illustrated in FIG. 28, in Case F, the first graphical display GR1 is displayed in the first area G8, in which the line L10 (the operable range of the operation handle 21) is displayed having a relatively short length and is shifted to the left side on the line L1 (the movable range of the arm 60), and the triangular mark MK (the current position of the arm 60) is displayed at the left end of the line L10 (the operable range of the operation handle 21). That is, the operation handle 21 has margins and can be rotated in both the left direction (the counterclockwise direction) and the right direction (the clockwise direction) by relatively small angles. Further, the arm 60 has no margin to the left and thus cannot be rotated to the left and has a margin to the right and thus can be rotated to the right. In Case F, it may be necessary to widen the operable range of the operation handle 21 to the right and to move the arm 60 to a position where the arm 60 can be moved in both the left and right directions.

Accordingly, the second graphical display GR2 is displayed in the second area G9, including the clutch operation graphical display a3, the arc a1 with the arrow a2 indicating to rotate the operation handle 21 in the counterclockwise direction by 360 degrees, and the value "360°." Then, the operator, who recognizes the second graphical display GR2 in the second area G2, rotates the operation handle 21 in the counterclockwise direction by 360 degrees while depressing the clutch pedal 22b (Operation 1), so that the operable range of the operation handle 21 is expanded to the right. Then, with this operation (Operation 1), the second graphical display GR2 is further displayed in the second area G9, including the arc a1 with the arrow a2 indicating to rotate the operation handle 21 in the clockwise direction by 360 degrees, and the value "360°." Then, the operator, who recognizes the second graphical display GR2 in the second area G2, rotates the operation handle 21 in the clockwise direction by 360 degrees without depressing the clutch pedal 22b (Operation 2), so that the arm 60 is rotated to the right. With this operation (Operation 2), the arm 60 is moved to a position where the arm 60 can be rotated in both the right and left directions, and thus the display of the second area G9 (the second graphical display GR2) disappears.

In a second embodiment, as described above, since the second graphical display GR2 is displayed for Operation 2 in addition to Operation 1, the operator can more easily recognize the required operation(s) of the operation handle 21. A second embodiment described above is particularly effective for an operator having a relatively low skill level.

[Modifications]

Note that one or more embodiments disclosed herein should be considered as exemplary in all respects and do not limit the invention. The scope of the invention is indicated by claims, not limited by explanation of one or more embodiments described above, and includes equivalents to the claims and all alterations (modifications) within the same.

For example, in first and second embodiments described above, the case has been described in which the image processing device 8 acquires the image from the endoscope 6 and generates the graphical user interface G. However, the invention is not limited thereto. For example, the control unit 31 of the medical manipulator 1, a control unit (not illustrated) of the remote control apparatus 2, or the like may generate the graphical user interface G. Further, an image processing device that acquires the image from the endoscope 6 and an image processing device that generates a graphical user interface G to be superimposed on the image from the endoscope 6 may be separately provided.

Further, in first and second embodiments described above, the case has been described in which the second graphical display GR2 indicates the required operation of the operation handle 21 to return the arm 60 to the inside of the movable range thereof and to return the operation handle 21 to the inside of the operable range thereof. However, the invention is not limited thereto. For example, the second graphical display GR2 may indicate only one of the required operation of the operation handle 21 to return the arm 60 to the inside of the movable range thereof and the required operation of the operation handle 21 to return the operation handle 21 to the inside of the operable range thereof.

Further, in first and second embodiments described above, the case has been described in which the second graphical display GR2 is displayed when the angle to the ends of the operable range of the operation handle 21 becomes equal to or less than the first threshold value and the second graphical display GR2 is displayed when the angle to the ends of the movable range of the arm 60 becomes equal to or less than the second threshold value. However, the invention is not limited thereto. For example, the second graphical display GR2 may be displayed only when the angle to the end of the operable range of the operation handle 21 is equal to or less than the first threshold value, or only when the angle to the end of the movable range of the arm 60 is equal to or less than the second threshold value. Further, the second graphical display GR2 may be displayed based on a reference(s) other than the first threshold value and the second threshold value.

Further, in first and second embodiments described above, the case has been described in which the first area G8L (the second area G9L) for the left arm 60L and the first area G8R (the second area G9R) for the right arm 60R are separately provided. However, the invention is not limited thereto. For example, the first area G8L for the left arm 60L and the first area G8R for the right arm 60R may be integrally or commonly provided, and the second area G9L for the left arm 60L and the second area G9R for the right arm 60R may be integrally or commonly provided.

Further, in first and second embodiments described above, the case has been described in which the first area G8L and the second area G9L for the left arm 60L are displayed on the left side in the monitor 24, and the first area G8R and the second area G9R for the right arm 60R are displayed on the right side in the monitor 24. However, the invention is not limited thereto. For example, the first area G8L and the second area G9L for the left arm 60L and the first area G8R and the second area G9R for the right arm 60R may be displayed side by side in the vertical direction in the monitor 24.

Further, in first and second embodiments described above, the case has been described in which the movable range of the arm 60 is indicted by the line (straight line) and the operable range of the operation handle 21 is indicated by the line (straight line). However, the invention is not limited thereto. For example, each of the movable range of the arm 60 and the operable range of the operation handle 21 may be displayed by a circular graph (arc), etc.

Further, in first and second embodiments described above, the case has been described in which the movable range of the arm 60 and the operable range of the operation handle 21 are displayed in the overlapping manner. However, the invention is not limited thereto. For example, the movable range of the arm 60 and the operable range of the operation handle 21 may be displayed being spaced away from each other.

Further, in first and second embodiments described above, the case has been described in which the second graphical display GR2 is represented by the arc a1 with the arrow a2 provided at the leading end of the arc a1 corresponding to the direction in which the operation handle 21 is to be rotated. However, the invention is not limited thereto. For example, the second graphical display GR2 may be represented by a linear arrow pointing a direction in which the operation handle 21 is to be rotated.

Further, in first and second embodiments described above, the first area G1 and the second area G2 are adjacent to (next to) each other. However, the invention is not limited thereto. For example, the first area G8 may be displayed on the left side (or right side) in the monitor 24, and the second area G9 may be displayed in the central region in the monitor 24.

Further, in first and second embodiments described above, the case has been described in which the number of the arms 60 provided is four. However, the invention is not limited thereto. In the invention, the number of the arms 60 may be any number as long as at least one is provided.

Further, in first and second embodiments described above, the case has been described in which each of the arm portion 61 and the positioner 40 are configured as the 7-axis articulated robot. However, the invention is not limited thereto. For example, each of the arm 61 and the positioner 40 may be configured as an articulated robot other than the 7-axis articulated robot (for example, a 6-axis articulated robot, an 8-axis articulated robot, or the like).

Further, in first and second embodiments described above, the case has been described in which the medical manipulator 1 includes the medical trolley 3, the positioner 40, and the arm base 50. However, the invention is not limited thereto. For example, the medical manipulator 1 may include only the arms 60 and not include the medical trolley 3, the positioner 40, and the arm base 50.

The functions of each of the elements disclosed herein may be carried out by a circuit or a processing circuit including a general purpose processor, a dedicated processor, an integrated circuit, an ASIC (Application Special Integrated Circuit), a conventional circuit, or a combination of two or more of them, that is configured or programmed to perform the functions. A processor is considered a processing circuit or a circuit because it contains transistors and other circuit elements. In the disclosure, a circuit, a unit, or a means may be either hardware that is configured to perform the recited function(s) or hardware that is programmed to perform the recited function(s). The hardware may be the hardware disclosed herein, or may be other known hardware that is programmed or configured to perform the described function(s). If the hardware is a processor which is considered as a type of a circuit, the circuit, means, or unit is a combination of hardware and software, and the software is used to configure the hardware and/or the processor.

The invention includes other embodiments or modifications in addition to one or more embodiments described above without departing from the spirit of the invention. The one or more embodiments described herein are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A robotic surgical system, comprising:
   an endoscope;
   a manipulator configured to support a surgical instrument;
   a remote control apparatus including a display device and an operation handle configured to operate the surgical instrument; and
   a control device configured to generate a graphical user interface and display, on the display device, the graphical user interface on an image captured by the endoscope, wherein
   the graphical user interface includes:
   a first area that displays a first graphical display indicating a movable range of the manipulator and an operable range of the operation handle in the movable range of the manipulator; and
   a second area different from the first area, wherein the second area displays, in response to determining that an angle from a current position of the operation handle to an end of the operable range of the operation handle is equal to or less than a first threshold value and/or an angle from a current position of the manipulator to an end of the movable range of the manipulator is equal to or less than a second threshold value, a second graphical display indicating a required operation to return the operation handle toward a center of the operable range of the operation handle and/or to return the manipulator toward a center of the movable range of the manipulator, the required operation indicated in the second graphical display including an indication whether a clutch operation to temporarily disconnect an operational connection between the manipulator and the operation handle is required and a direction to rotate the operation handle.

2. The robotic surgical system according to claim 1, wherein the surgical instrument is a first surgical instrument,
the manipulator is a first manipulator configured to support the first surgical instrument,
the operation handle is a first operation handle configured to operate the first surgical instrument,
the robotic surgical system further includes a second manipulator configured to support a second surgical instrument and a second operation handle configured to operate the second surgical instrument, and
the first area that displays the first graphical display is provided for each of the first manipulator and the second manipulator, and the second area that displays the second graphical display is provided for each of the first manipulator and the second manipulator.

3. The robotic surgical system according to claim 2, wherein the first operation handle is arranged on one side in a left-right direction of the remote control apparatus and the second operation handle is arranged on the other side in the left-right direction of the remote control apparatus,
the first area and the second area for the first manipulator are displayed on the one side in the left-right direction on the display device, and
the first area and the second area for the second manipulator are displayed on the other side in the left-right direction on the display device.

4. The robotic surgical system according to claim 1, wherein the first graphical display further indicates a current position of the manipulator in the operable range of the operation handle, in addition to the operable range of the operation handle and the movable range of the manipulator.

5. The robotic surgical system according to claim 1, wherein the first graphical display displays a line representing the movable range of the manipulator and a line representing the operable range of the operation handle, and
the control device is configured to expand and contract a length of the line representing the operable range of the operation handle in response to movement of the operation handle while a length of the line representing the movable range of the manipulator being fixed.

6. The robotic surgical system according to claim 5, wherein the line representing the operable range of the operation handle and the line representing the movable range of the manipulator are displayed in such an overlapped manner that an amount of deviation between the operable range and the movable range can be identified, and
the line representing the operable range of the operation handle is displayed being biased with respect to the line representing the movable range of the manipulator in a deviation direction in which the operable range of the operation handle is deviated from the movable range of the manipulator, in such a manner that the deviation direction can be identified.

7. The robotic surgical system according to claim 5, wherein the line representing the movable range of the manipulator is displayed with a mark indicating the center of the movable range of the manipulator.

8. The robotic surgical system according to claim 1, wherein the second graphical display displays an arc with an arrow at a leading end of the arc indicating the direction in which the operation handle is to be rotated.

9. The robotic surgical system according to claim 8, wherein the arc has a length corresponding to a rotation angle in which the operation handle is to be rotated.

10. The robotic surgical system according to claim 1, wherein the second area further displays a value of a rotation angle in which the operation handle is to be rotated.

11. The robotic surgical system according to claim 1, wherein the remote control apparatus further comprises an input device to perform the clutch operation to temporarily disconnect the operational connection between the manipulator and the operation handle.

12. The robotic surgical system according to claim 11, wherein the control device is configured, when the input device is operated, to display the second graphical display.

13. The robotic surgical system according to claim 1, wherein the control device is configured, when a connecting operation is performed to connect the manipulator and the operation handle, to display the second graphical display.

14. The robotic surgical system according to claim 1, wherein the control device is configured to display the first area and the second area to be adjacent to each other.

15. The robotic surgical system according to claim 1, wherein the control device is configured to switch between a mode in which the first graphical display and the second graphical display are displayable and a mode in which the first graphical display and the second graphical display are not displayable.

16. A control device to be used in a robotic surgical system that comprises an endoscope, a manipulator configured to support a surgical instrument, and a remote control apparatus including an operation handle configured to operate the surgical instrument and a display device, wherein
the control device is configured to generate a graphical user interface and display, on the display device, the graphical user interface on an image captured by the endoscope in an overlapped manner, and
the graphical user interface includes:
a first area that displays a first graphical display indicating a movable range of the manipulator and an operable range of the operation handle in the movable range of the manipulator; and
a second area different from the first area, wherein the second area displays in response to determining that an angle from a current position of the operation handle to an end of the operable range of the operation handle is equal to or less than a first threshold value and/or an angle from a current position of the manipulator to an end of the movable range of the manipulator is equal to or less than a second threshold value, a second graphical display indicating a required operation to return the operation handle toward a center of the operable range of the operation handle and/or to return the manipulator toward a center of the movable range of the manipulator, the required operation indicated in the second graphical display including an indication whether a clutch operation to temporarily disconnect an operational connection between the manipulator and the operation handle is required and a direction to rotate the operation handle.

17. A display method performed by a control device in a robotic surgical system, wherein the robotic surgical system includes: an endoscope; a manipulator configured to support a surgical instrument; a remote control apparatus including an operation handle configured to operate the surgical instrument and a display device; and the control device, the method comprising:

acquiring an image captured by the endoscope; and
generating a graphical user interface and displaying, on the display device, the graphical user interface on the image captured by the endoscope in an overlapped manner, wherein the graphical user interface displays, in a first area, a first graphical display that indicates a movable range of the manipulator and an operable range of the operation handle in the movable range and displays, in a second area different from the first area, in response to determining that an angle from a current position of the operation handle to an end of the operable range of the operation handle is equal to or less than a first threshold value and/or an angle from a current position of the manipulator to an end of the movable range of the manipulator is equal to or less than a second threshold value, a second graphical display that indicates a required operation to return the operation handle toward a center of the operable range of the operation handle and/or to return the manipulator toward a center of the movable range of the manipulator, the required operation indicated in the second graphical display including an indication whether a clutch operation to temporarily disconnect an operational connection between the manipulator and the operation handle is required and a direction to rotate the operation handle.

* * * * *